US012788678B2

(12) United States Patent
Nurse et al.

(10) Patent No.: US 12,788,678 B2
(45) Date of Patent: Nov. 10, 2026

(54) WEARABLE BLISTER CARD MAGAZINES, BLISTER CARD TRANSFER TRAYS AND SYSTEMS, AND MEDICATION MAGAZINES AND INTELLIGENT MEDICATION MANAGEMENT SYSTEMS

(71) Applicants: Lloyd Cleveland Nurse, Decatur, GA (US); Darien Okinza Nurse, Brooklyn, NY (US)

(72) Inventors: Lloyd Cleveland Nurse, Decatur, GA (US); Darien Okinza Nurse, Brooklyn, NY (US)

( * ) Notice: Subject to any disclaimer, the term of this patent is extended or adjusted under 35 U.S.C. 154(b) by 57 days.

(21) Appl. No.: 19/070,427

(22) Filed: Mar. 4, 2025

(65) Prior Publication Data

US 2025/0195330 A1 Jun. 19, 2025

Related U.S. Application Data

(63) Continuation-in-part of application No. 17/739,559, filed on May 9, 2022, now Pat. No. 12,239,604.

(51) Int. Cl.

*G16H 20/13* (2018.01)
*A61J 1/03* (2023.01)
*A61J 7/04* (2006.01)

(52) U.S. Cl.

CPC ............. *A61J 1/035* (2013.01); *A61J 7/0418* (2015.05); *G16H 20/13* (2018.01)

(58) Field of Classification Search

CPC ............................... G16H 20/13; A61J 7/0418
See application file for complete search history.

(56) References Cited

U.S. PATENT DOCUMENTS 9,027,787 B2 * 5/2015 Eriksson .................. A61J 1/03
221/83
10,650,661 B2 5/2020 Mehregany
(Continued)

FOREIGN PATENT DOCUMENTS

DE 2416632 A1 4/1975

OTHER PUBLICATIONS

International Search Report and Written Opinion issued in PCT Application No. PCT/US2023/021460 on Jul. 27, 2023.
(Continued)

*Primary Examiner* — Gene O Crawford
*Assistant Examiner* — Ayodeji H Ojofeitimi
(74) *Attorney, Agent, or Firm* — LeonardPatel PC; Michael A. Leonard, II; Sheetal S. Patel

(57) ABSTRACT

Wearable blister card magazines, blister card transfer trays and systems, and standalone medication magazines including one or more compartments that hold respective sleeves of medication, as well as a respective blister card, are provided. The blister card(s) include blisters of medication, and the blister sleeve(s) include openings designed to align with the blisters of the blister card(s). The removal of medication from each blister may be automatically detected and digitally recorded, along with the time and the individual who removed the medication. In addition to permitting alignment of each blister on the blister card, the openings on the sleeve also permit the ejection of the medicine through the openings without being removed from the sleeve. Intelligent medication management systems configured to provide end-to-end management and monitoring for patient dosing regimens are also provided.

20 Claims, 25 Drawing Sheets

(56) References Cited

U.S. PATENT DOCUMENTS

| | | | | |
|---|---|---|---|---|
| 11,672,740 | B1 * | 6/2023 | Norman | A61J 1/03<br>340/539.1 |
| 2009/0139893 | A1 | 6/2009 | McGonagle et al. | |
| 2011/0163156 | A1 | 7/2011 | Smith et al. | |
| 2013/0018503 | A1 | 1/2013 | Carson et al. | |
| 2013/0082581 | A1 | 4/2013 | Bufalini et al. | |
| 2016/0022541 | A1 * | 1/2016 | Dalal | A61J 7/0084<br>221/9 |
| 2016/0158107 | A1 * | 6/2016 | Dvorak | A61J 7/0084<br>221/9 |
| 2016/0176617 | A1 | 6/2016 | Bolognia et al. | |
| 2017/0071827 | A1 | 3/2017 | Stevens | |
| 2017/0294105 | A1 | 10/2017 | Mehregany et al. | |
| 2018/0075216 | A1 | 3/2018 | Nurse et al. | |
| 2019/0103181 | A1 | 4/2019 | Lesau et al. | |
| 2019/0117509 | A1 | 4/2019 | Hiraizumi et al. | |
| 2019/0378602 | A1 | 12/2019 | Latorraca et al. | |
| 2021/0298994 | A1 | 9/2021 | Liu et al. | |
| 2022/0028515 | A1 | 1/2022 | Amoyal et al. | |
| 2022/0273516 | A1 * | 9/2022 | Kwon | A61J 7/0481 |

OTHER PUBLICATIONS

Mohamed Barakat, “Final Office Action”, issued May 29, 2024, U.S. Appl. No. 17/739,559.
Mohamed Barakat, “Non-Final Office Action”, issued Feb. 16, 2024, U.S. Appl. No. 17/739,559.
Mohamed Barakat, “Notice of Allowance”, issued Nov. 27, 2024, U.S. Appl. No. 17/739,559.

* cited by examiner

800

WEARABLE BLISTER CARD MAGAZINES, BLISTER CARD TRANSFER TRAYS AND SYSTEMS, AND MEDICATION MAGAZINES AND INTELLIGENT MEDICATION MANAGEMENT SYSTEMS

CROSS REFERENCE TO RELATED APPLICATION

This application is a continuation-in-part (CIP) of, and claims the benefit of, U.S. Nonprovisional patent application Ser. No. 17/739,559, which issued as U.S. Pat. No. 12,239,604 on Mar. 4, 2025. The subject matter of this earlier filed application is hereby incorporated by reference in its entirety.

FIELD

The present invention generally relates to medication management, and more specifically, to wearable blister card magazines, blister card transfer trays and systems, and standalone medication magazines including one or more compartments that hold respective sleeves and blister cards containing medication and intelligent medication management systems.

BACKGROUND

As the state of the art of healthcare continues to evolve, people are increasingly aware of the need to explore the benefits of medications and the varying effects on individuals. Race, culture, geography, and other elements play a role in the efficiency and effectiveness of a given medication. It would therefore be beneficial to study and understand the effect of each dose of medication on a given person. The quantity of medication, time of administration, method of administration, and interaction with other substances within the body can be significant contributing factors to the precision and effectiveness of medications for a given individual.

The challenge of providing timely notifications and instructions to safely consume each dose of authenticated medication in the original prescribed or packaged containers using the identification of a specific user to access and consume a required dose, confirm that the dose(s) were taken, and automatically recording each action in the process with the aid of on-screen instructions on a suitable device, for example, has yet to be effectively solved. Real-time notification and recording of medicine usage data for all medicines simultaneously, and potentially intervention, to ensure optimum results and avoid episodic events is desirable.

Also, pharmacists are burdened with the responsibility of communicating with patients and coordinating with insurers and care teams to ensure that drugs dispensed achieve their intended purpose. Preauthorization can be simplified, automated and made more efficient. There are numerous considerations in addition to side effects, adverse reactions and compatibility of drugs and patients especially when multiple chronic diseases exist. There is also a need for tools to help the pharmacist and patient interaction to be better synchronized by passing some of the responsibility onto the patient. Ensuring accountability, especially in the use of opioids and advanced therapeutics, requires new tools. The need to track a specific pill or specific pills in a multiple dosing regimen can be of considerable value. Each pill may have a story, and that should be told to advance the targeting of specific drugs in precision medicine.

An example of this challenge is the need for a pharmacist to secure opioids in a double locking system and ensure that each pill is counted and then placed in a container to be given to a patient. One missing pill may be a reason for the pharmacist to write and file a report to the U.S. Drug Enforcement Agency (DEA) and may evoke fines and discipline for recurring offenses. The process is time consuming for pharmacists with associated risks. Furthermore, a patient may misuse the medication in many ways, including selling the entire container to a drug dealer. The implications of this misuse are far more dangerous than a miscount by a pharmacist, but misuse often goes unchecked, leading to increased addiction and death. Accordingly, an improved and/or alternative approach to medication management may be beneficial.

SUMMARY

Certain embodiments of the present invention may provide solutions to the problems and needs in the art that have not yet been fully identified, appreciated, or solved by current medication management technologies, and/or an alternative solution thereto. For example, some embodiments of the present invention pertain to wearable blister card magazines, blister card transfer trays and systems, and standalone medication magazines including one or more compartments that hold respective sleeves and blister cards containing medication and intelligent medication management systems.

In an embodiment, a medication management system includes one or more trays that include a plurality of compartments. Each compartment of the one or more trays is configured to store a respective blister card and includes a sensor or switch. The one or more trays also include an indicator for each compartment in the one or more trays and a contact point for each compartment in the one or more trays. The medication management system also includes a cabinet that includes a plurality of indicators for each of the one or more trays and a plurality of recesses for each of the one or more trays. The cabinet also includes a plurality of harnesses located in respective recesses of the plurality of recesses. The plurality of harnesses include a plurality of contact points for each contact point of the one or more trays. The plurality of contact points of the harness are configured to align with the respective contact points of the one or more trays when a respective tray of the one or more trays is inserted into the cabinet.

In another embodiment, a medication management system includes one or more trays that include a plurality of compartments. Each compartment of the one or more trays is configured to store a respective blister card and includes a sensor or switch. The one or more trays also include an indicator for each compartment in the one or more trays and a contact point for each compartment in the one or more trays. The medication management system also includes a cabinet that includes a plurality of indicators for each of the one or more trays and a plurality of recesses for each of the one or more trays. The cabinet also includes a plurality of harnesses located in respective recesses of the plurality of recesses. The plurality of harnesses include a plurality of contact points for each contact point of the one or more trays. The plurality of contact points of the harness are configured to align with the respective contact points of the one or more trays when a respective tray of the one or more trays is inserted into the cabinet. The medication management system further includes a cabinet computing system, a pharmacy computing system, a medication magazine, and a mobile device. The mobile device is configured to inform a user that a dose of a medication should be taken. The medication magazine is configured to track access to and removal of a dose from a blister card stored in the medication magazine and confirm whether an appropriate dose was taken and inform the mobile device. The mobile device is configured to inform the pharmacy computing system of a status of the dose.

In yet another embodiment, a medication management system includes one or more trays that include a plurality of compartments. Each compartment of the one or more trays is configured to store a respective blister card and includes a sensor or switch. The one or more trays also include an indicator for each compartment in the one or more trays and at least one contact point on the one or more trays. The medication management system also includes a cabinet that includes a plurality of indicators for each of the one or more trays and a plurality of recesses for each of the one or more trays. The cabinet also includes a plurality of harnesses located in respective recesses of the plurality of recesses. The plurality of harnesses include at least one respective contact point for each contact point of the one or more trays. The at least one contact point of the harness is configured to align with the respective at least one contact point of the one or more trays when a respective tray of the one or more trays is inserted into the cabinet. The medication management system further includes a cabinet computing system configured to track statuses of the cabinet.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

Unless otherwise indicated, similar reference characters denote corresponding features consistently throughout the attached drawings.

DETAILED DESCRIPTION OF THE EMBODIMENTS

Figure 1A:
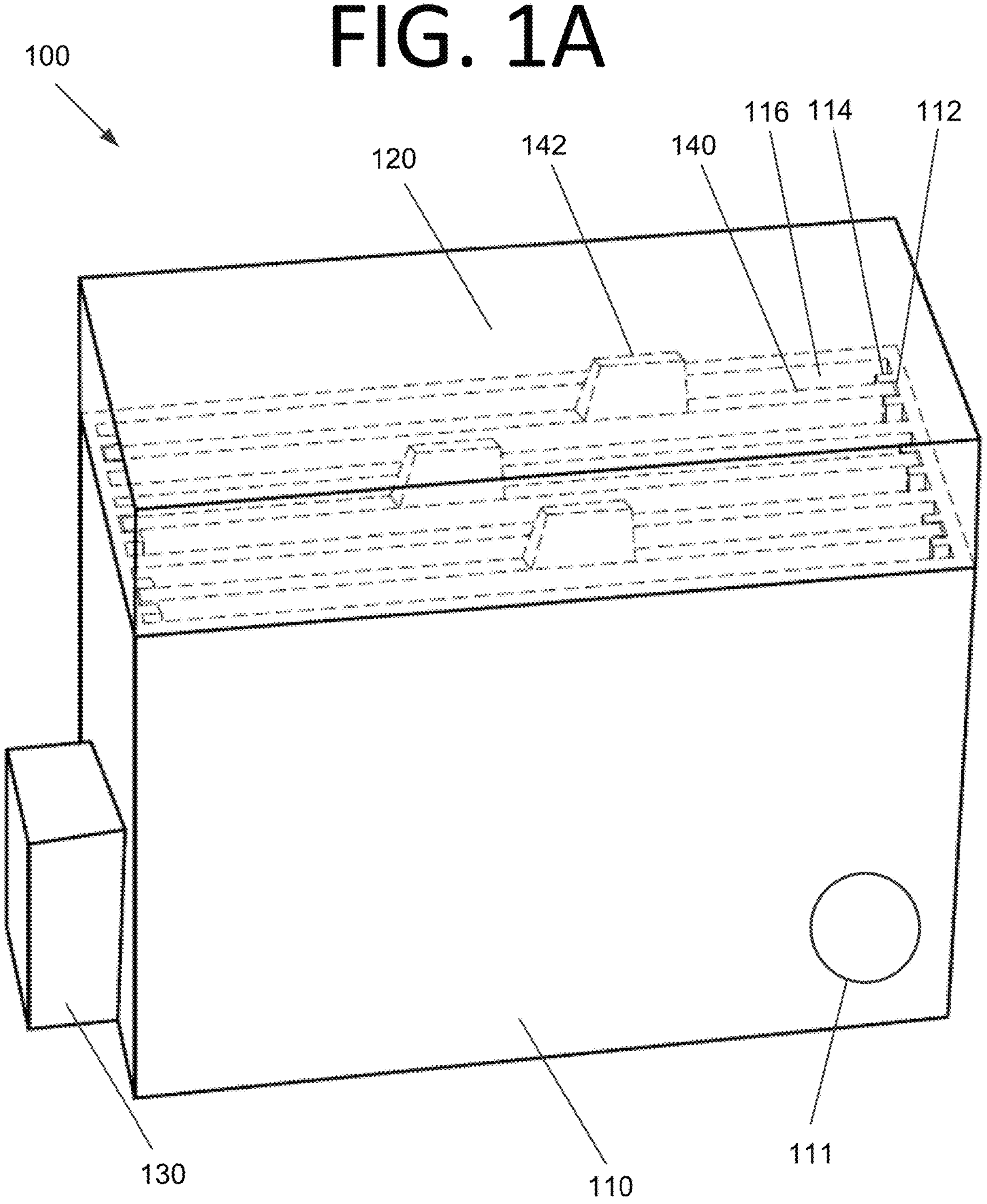
FIG. 1A is a perspective view illustrating a medication magazine, according to an embodiment of the present invention.

Some embodiments pertain to wearable blister card magazines, blister card transfer trays and systems, and standalone medication magazines including one or more compartments that hold respective sleeves of medication, as well as a respective blister card. The blister card includes blisters of medication, and the blister sleeve includes openings designed to align with the blisters of the blister card. In addition to permitting alignment of each blister on the blister card, the openings on the sleeve also permit the ejection of the medicine through the openings without being removed from the sleeve. Certain embodiments pertain to an intelligent medication management system that is configured to provide end-to-end management and monitoring for patient dosing regimens. The ability provided by some embodiments to record and remotely see when a specific pill has been removed is a significant advantage that is not provided by current systems. For instance, such embodiments may notify, instruct, and automatically provide a recorded video option regarding the use of specific pills or doses of medication to aid the tailoring of a treatment plan to a specific individual. Also, casualties due to medications may be reduced by remotely and strategically weaning a patient off of potentially dangerous drugs and onto safer alternatives using the system of some embodiments.

Pill blister packs are often used as a mechanism to simplify the process of helping users to remember what pill of medication to take, when to take the pill, and to provide visual confirmation that a specific dose has been taken or missed. This may be accomplished by providing time and day markings on blister cards adjacent to each blister or row of blisters that may contain one or more pills of medication. Blister packs also provide an airtight seal that helps to preserve the efficacy of the medicine. Additionally, blister packs are often made with material that is difficult for children to open. However, this childproofing has the unintended consequence of also making the medication difficult for some disabled or elderly adults to access.

In some institutional care settings, nurses are required to refer to a patient's medication chart, find the correct blister card from out of a drawer of sometimes many cards, eject the appropriate pill(s) from the blister pack(s), administer the dose(s) of medication, and manually record that the dosing was taken and provide a signature for confirmation. Some hospitals have upgraded systems that require the scanning of each blister pack and the patient's wristband to confirm that a specific pill was given to the correct patient each and every time that a pill is to be taken. However, both of these time-consuming processes rely on the staff member doing so correctly. It would be beneficial to further simplify and definitively determine how each blister in a blister card or stored individually (i.e., a single dose blister) is used, as well as to digitally record usage automatically. It would also be beneficial to reduce the error of picking up the wrong blister card or unintentionally missing doses.

Some embodiments provide such advantages automatically. For instance, in some embodiments: (1) The exact location of each blister card and blister enables accurate tracking of each pill; (2) Relevant individual(s) can be automatically notified when a blister card or blister is accessed; (3) The identity of the person accessing the blister card or blister can be confirmed; (4) The time of access by person who accesses the blister card or blister can be automatically recorded; (5) Medications can be accurately confirmed and instructions can be provided via a display on any number of activities performed with blister cards or medication; (6) A foolproof mechanism of ensuring the replacement of a blister card into the assigned location within a magazine can be provided; (7) Another blister card can be selected and used in the same manner when multiple cards are to be used; (8) A video recording of each dosing event may be provided; and/or (9) The integrity of the dosing regimen may be reliably ensured. Various types of medications may be stored and administered in this manner including, but not limited to, pills, capsules containing liquid or powder, or any other suitable medication delivery system without deviating from the scope of the invention.

Unlike existing vending and inventory management systems, some embodiments employ a different methodology of data collection and allow for the repeated usage of a single blister card, as well as how each blister on the card is counted. In certain embodiments, each depleted blister may be automatically confirmed after use. In some embodiments, who accesses and replaces the card into a magazine and when is recorded. In certain embodiments, assurance is provided that each card or sleeve is replaced into its assigned slot in a magazine. In some embodiments, the predetermined scheduling of medication dosing events may be provided and notifications may be provided to a patient or caretaker to access the blister card and provide the scheduled dose of medicine.

In some embodiments, light and/or sound may be used to identify the correct blister sleeve that is to be removed. In certain embodiments, the appropriate sleeve may be partially released, but remain under locked access until an authorized user provides access credentials and removes the sleeve from the magazine. This may be particularly useful for the visually impaired.

Verification that a blister has been depleted may be provided in various ways including, but not limited to: (1) Providing a light-sensitive board and with lights (and potentially light sensors) on a side of the sleeve, where light is received by the board through each depleted blister and a count is recorded; (2) Providing blister cards with conduction seals that can be identified and counted when the conduction seal is broken; and/or (3) Attaching a separate counter card to each blister card and sleeve, where the counter card provides an indication to the system when each blister is depleted. As used herein, a "conduction seal" is defined as wires passing through blisters of a blister card. When a wire for a given blister is broken by opening the blister, this prevents current from being passed through the wire, which informs an associated controller that a given pill was taken. Other information, such as the location of a given blister and a time that the connection was broken may be recorded. This may be facilitated by individual blister wires connected in series or by parallel connections.

Various benefits may be realized. For instance, in some embodiments, the recording of accurate real-time medication usage information may be compared to real-time vital sign readings so that dosage of the medication can be corrected, if necessary, in a timely manner. For instance, if a patient's blood pressure is higher than expected and remains so through multiple dosing times, the strength of the medication may be increased. Data may be provided with respect to multiple medications used by multiple individuals with multiple conditions. This information may be analyzed using artificial intelligence (AI) and/or machine learning (ML) to determine potential synergies between medications and provide more effective dosing regimens.

The medication magazine of some embodiments includes one or more compartments. Each compartment is configured to hold a respective blister sleeve and a respective blister card. Each blister card includes blisters of medication, and the blister sleeve includes openings designed to align with the blisters of the blister card. In addition to permitting alignment of each blister on the blister card, the openings on the sleeve also permit the ejection of the medicine through the openings without being removed from the sleeve.

In some embodiments, an associated computing system is provided. The computing system may be a smart phone, a laptop or desktop computer, an Internet-of-Things (IoT) device, a part of the magazine itself, or any other suitable computing device without deviating from the scope of the invention. The magazine may have its own electronics configured to communicate with the computing system and control operation of the magazine in some embodiments. This computing system may include a display so it can more effectively convey information to users. Blister cards may be scanned (e.g., a barcode, a QR code, etc.) or manually entered into the computing system (e.g., a serial number on the blister card). The computing system may automatically assign medication sleeves to a specific compartment in the magazine in some embodiments and may cause one or more lights adjacent to that location to glow or blink so the compartment can be readily identified by the user. Alternatively, inserting the blister sleeve into the compartment may cause the computing system to perform the assignment. When the sleeve is inserted, the light(s) may stop glowing or blinking. The sleeve is thus assigned to and associated with that compartment.

The computing system may track the appropriate information for that compartment/sleeve/card (e.g., number of doses, location in the blister card of the next dose, dosing time, etc.) and inform authorized user(s) to access the appropriate dose at the appropriate time. An authorized user may be required to provide credentials (e.g., providing a security code, a username/password, canning a thumbprint, authorization via facial recognition, etc.) to gain access to the blister sleeve and card. In some embodiments, the computing system and/or magazine indicate the quantity and location of blisters to be accessed. The user may then be required to replace that sleeve within its assigned compartment to complete the dosing process. In some embodiments, access to multiple compartments may be required to administer multiple medications.

When the sleeve and card are replaced into their assigned compartment, the computing system and/or magazine electronics may count and verify the number and location of empty blisters. This information may be logged and sent to a remote system (e.g., a local or cloud-based management system) where care professionals can access the information. Thus, remote tracking by trained professionals may also be provided.

Some embodiments may have applications beyond medicine. For instance, tracking of items without associated electronics may be provided for IoT devices configured as a magazine.

Blister cards used in medication administration and storage have various potential advantages over pill bottles and packages. Time to use markings and individual seals have helped to reduce overdosing and improved efficacy, but many challenges remain. Timely notification for dosing administration, verification of correct dosage taken, authentication of a user identifier (ID), authentication of drugs to verify authenticity, and other concerns are still challenges in this field. Some embodiments attempt to address some or all of these challenges as they relate to proposed regulations from the U.S. Food and Drug Administration (FDA) related to blister packaging of opioids and other potentially dangerous medications to help to control prescribing and dispensing, which can be pathways to misuse, abuse, addiction, and death.

Regarding the responsibilities placed on pharmacists with respect to controlled substances, this upside down responsibility can be better mitigated by the use of the blister card transfer trays and systems disclosed herein, where access and removal of each pill by a patient is monitored by a digital process that identifies instances of misuse and confirms compliance. The pharmacist may still have the cumbersome task of securing and counting each pill, however. To this end, some embodiments remove this requirement and improve the efficiency of the pharmacy process.

Some embodiments make it easier to perform inventory control, storage, and transfer of medication from the manufacturer to the pharmacy and to eliminate the need for multiple recounts of individual pills. Such embodiments can enable the smooth error-free transfer of blister cards to a patient's blister card magazine, where the access and removal of each pill by a patient is monitored by a digital process that identifies misuse and confirms compliance. The pharmacist is released from the cumbersome task of counting and security is a smooth and efficient process. To this end, the pharmacy process can be made significantly more productive.

A tray with slots holds multiple blister cards in some embodiments. Blister cards may be enclosed in a sleeve in some embodiments, but in certain embodiments, the blister cards may be constructed from a rigid and potentially biodegradable material that removes the need for a sleeve. Each slot in the tray may include a sensor or electrical contact that senses the removal of each blister card and records removal in associated software in a pharmacy and patient account, for example. The same card may have a unique tag or identifier that confirms its placement into a compartment of the blister card magazine. Errors or missing pills can be automatically identified by the medication magazine and addressed. In some embodiments, a wearable and mobile blister card magazine is then given to the patient. The patient is notified via a smart phone or some other computing system (e.g., a tablet, a smart watch, etc.) to access the magazine and take a dose, which is recorded in real time or near-real time in the patient's account. The blister card magazine may have a belt or holster for wearing on the body to increase the difficulty of theft.

The populated blister cards may be delivered from the manufacturer in a locked, tamperproof tray with a hinged or slidable cover. The tray can then be inserted into a drawer-type compartment of a secured cabinet that records the existence of that uniquely identifiable tray. The tray may contain unit dosing blister cards for a specific need, such as dental pain after oral surgery, which may be a three day supply of opioids. Another tray may contain blister cards for patients with chronic diseases in long term and sometimes terminal conditions. Such trays may contain a 30 day supply of opioids, for example. This system of the tray, blister card, and medication magazine, along with the increased tendency for patent compliance resulting therefrom, will mitigate many of the challenges that exist in medication usage. In some embodiments, device-to-device data is provided for advancing AI with additional possibilities for machine learning and digital twins.

FIG. 1A is a perspective view illustrating a medication magazine 100, according to an embodiment of the present invention. Medication magazine 100 includes a body 110, a cover 120, and electronics 130. The interior space defined by body 110 forms one or more "compartments" in this embodiment. As used herein, a compartment is defined as a space within a magazine that is designed to house a respective blister sleeve. Electronics 130 may include various hardware components, such as a processor or controller, a transceiver, memory, a bus system, a sound card, a speaker, and/or any other suitable hardware components without deviating from the scope of the invention. In certain embodiments, electronics 130 may include similar components to at least some of those of computing system 300 of FIG. 3. Electronics 130 may also include control software that controls operation of electronics 130 and any components connected thereto, such as lights, an external speaker, etc.

Figure 1B:
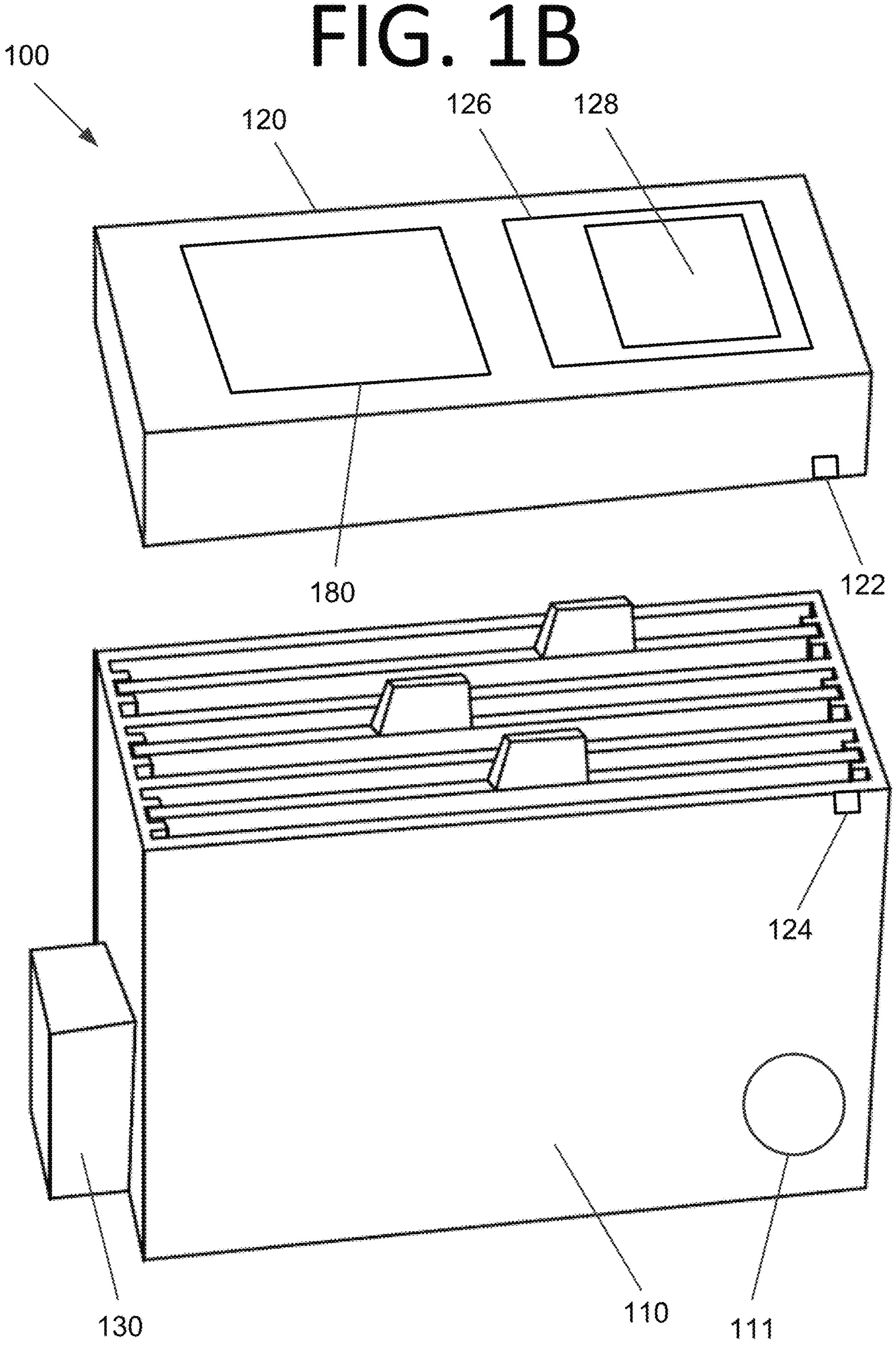
FIG. 1B is a perspective view illustrating the medication magazine with a separated cover, according to an embodiment of the present invention.

In some embodiments, cover 120 may be a hinged locking cover including a lock that is secured by an authentication device 126 (see FIG. 1B). In this embodiment, authentication device 126 as a biometric authentication device that includes a fingerprint scanner 128. However, any suitable authentication device, whether electronic, mechanical, or both, may be used without deviating from the scope of the invention. Authentication device 126 may be operably connected to electronics 130.

Authentication device 126 or electronics 130 may control operation of a lock that includes a cover portion 122 and a body portion 124. A speaker 111 operably connected to electronics 130 provides audio notifications and alerts. In some embodiments, speaker 111 may provide escalating and increasingly urgent notifications if cover 130 is not unlocked and medication is not removed, taken, and replaced after a period of time. For instance, the alert may become louder, speech via the speaker may become more urgent, etc.

Body 110 includes slots 112 defined by teeth 114 that provide locations for individual blister sleeves 140 within body 110. In this embodiment, each blister sleeve 140 includes a tab 142 that facilitates easy removal of blister sleeves 140 from slots 112 and insertion back into slots 112 after use. In this embodiment, separator gaps 116 are provided between blister sleeves 140. However, in some embodiments, separator gaps 116 may not be present to facilitate a more compact design and/or to house more blister sleeves 140.

A scanner 180 scans the unique identifier associated with blister cards 170 in this embodiment. However, in some embodiments, scanning functionality may be provided via an application running on a smart phone, tablet, laptop computer, etc. that is capable of communicating with electronics 130. Electronics 130 may assign blister cards to respective blister sleeves, and further assign blister sleeves to respective locations in body 110. Electronics 130, via hardware or software, may not permit users to place an assigned blister sleeve in a different location. In some embodiments, medication magazine 100 or an external smart phone, tablet, laptop computer, etc. may display the state of each blister, sleeve, and compartment (i.e., the location of body 110 in which each blister sleeve 140 is inserted). In certain embodiments, medication magazine 100 or computing systems such as those shown in FIG. 2 may offer a video providing instruction on the use of specific pills or doses of medication that may aid the tailoring of a treatment plan to a specific individual, potentially with with direct reference to genetic sequencing, nuclear medicine, other precision sciences, or telemedicine content for that individual, if available.

Figure 1C:
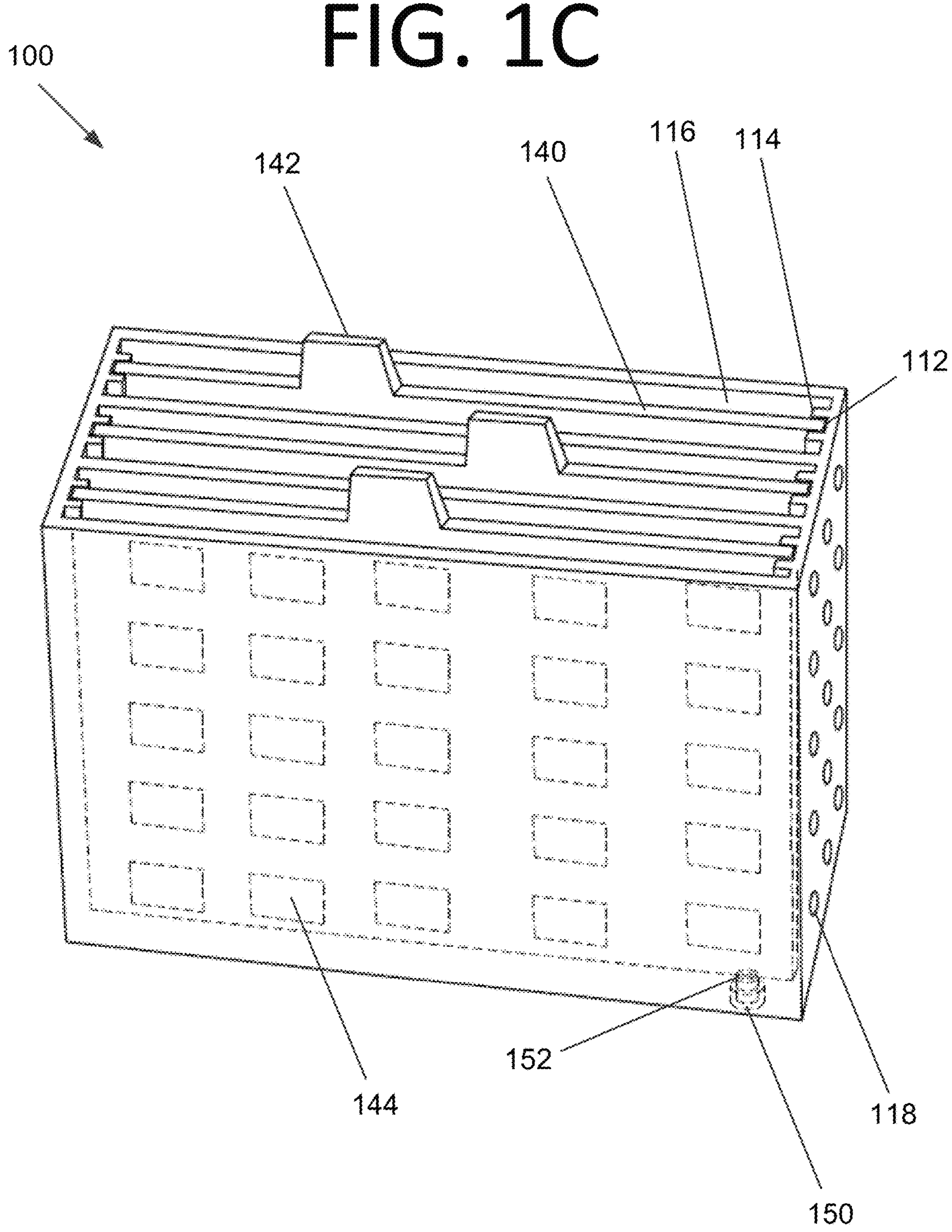
FIG. 1C is a perspective view illustrating the medication magazine without the cover, according to an embodiment of the present invention.
Figure 1D:
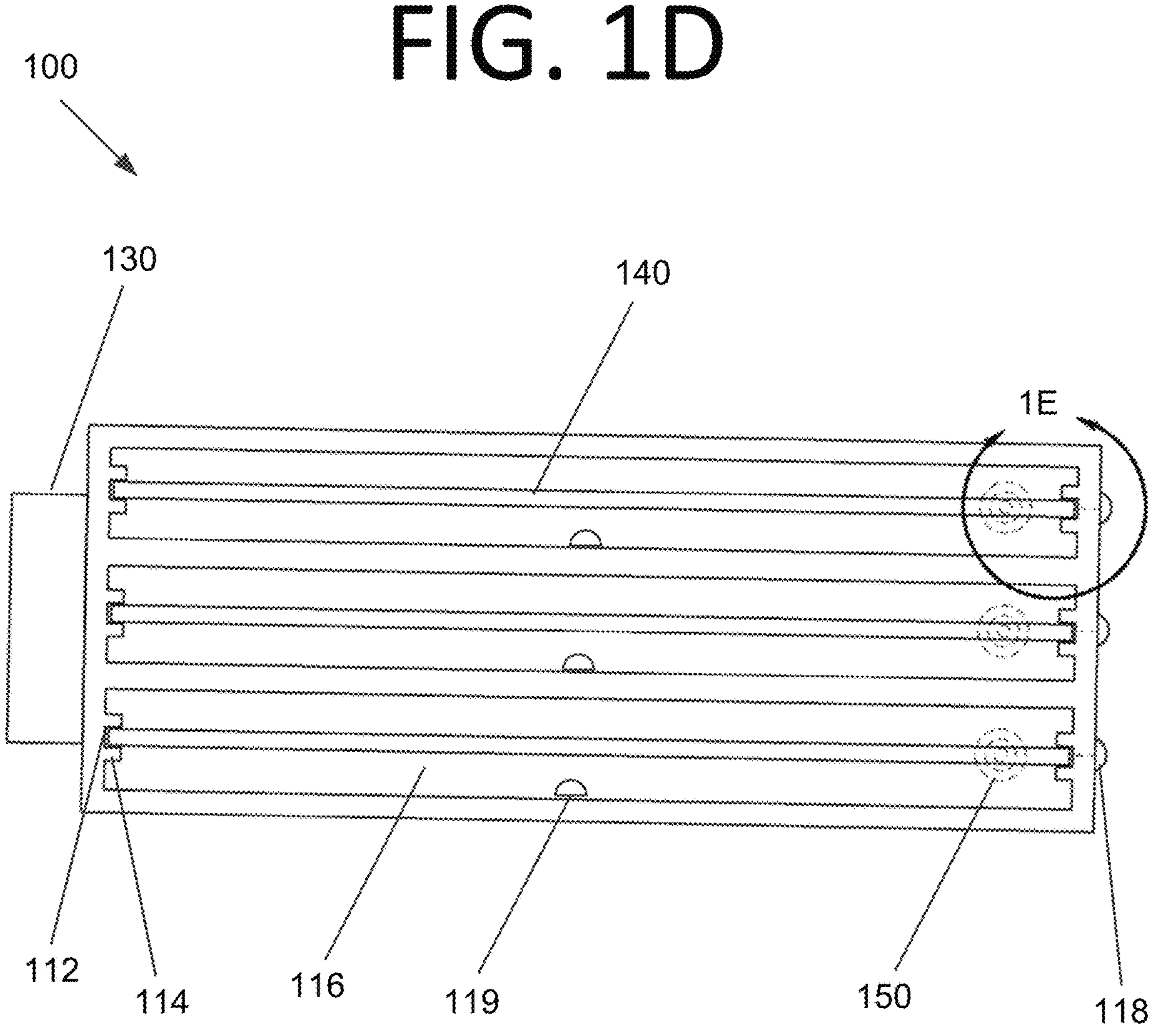
FIG. 1D is a top view illustrating the medication magazine with the cover removed, according to an embodiment of the present invention.
Figure 1E:
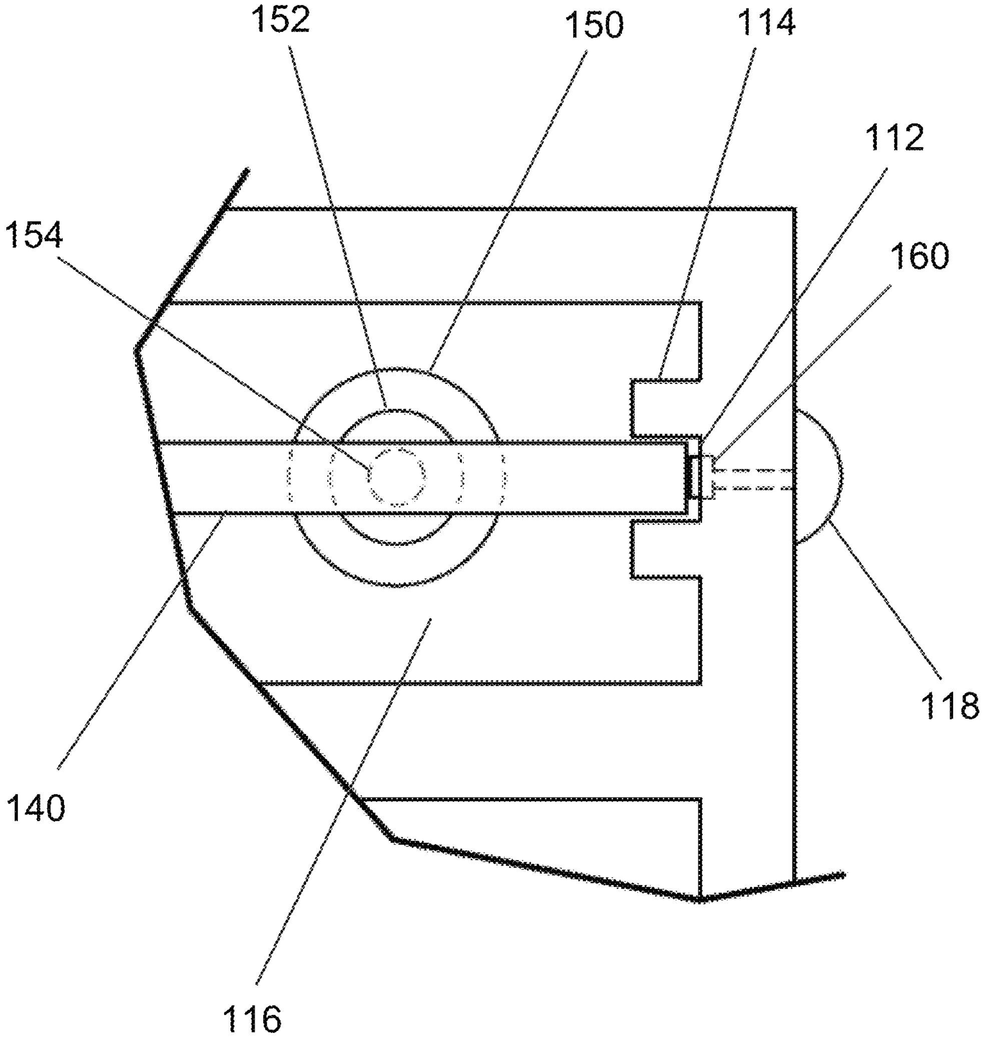
FIG. 1E is a top view illustrating a portion of the medication magazine, according to an embodiment of the present invention.
Figure 1F:
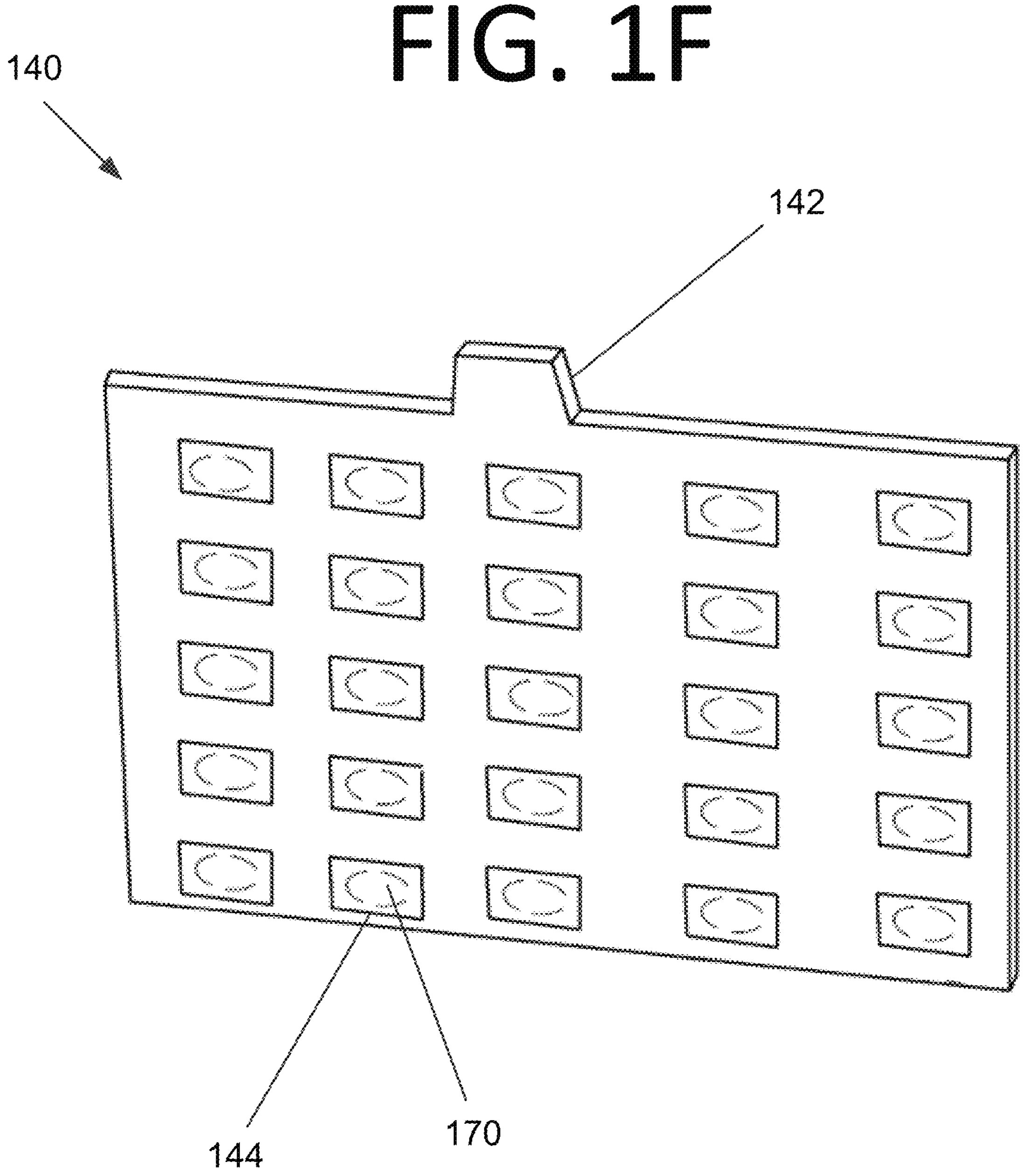
FIG. 1F is a perspective view illustrating a blister sleeve containing a blister card, according to an embodiment of the present invention.

Referring to FIGS. 1C and 1D, each blister sleeve 140 includes openings 144 that correspond to respective blisters in a blister card housed therein (see, e.g., FIG. 1F). Individual blisters are accessible via openings 144. In some embodiments, openings 144 may have a removable or slidable cover (not shown).

In this embodiment, medication magazine 100 includes lights 118 for respective blister sleeves 140 that are located on body 110. Electronics 130 may cause lights to glow or blink at a time when a medication in a blister sleeve 140 should be taken. In some embodiments, the lights indicate which compartment should be accessed. The lights may stay lit until associated blister sleeve 140 is removed and replaced. In addition to lights, a spring-loaded lock (e.g., lock 150) may release respective blister sleeve 140 such that blister sleeve 140 is above other blister sleeves 140 that are still inserted in magazine 100. In this manner, unlocked blister sleeve 140 protrudes outward from body 110. This may assist individuals with visual impairments in identifying the correct blister sleeve via touch.

A spring-loaded lock 150 for each blister sleeve 140 is also included in this embodiment. Spring-loaded lock 150 is operably connected to control electronics and allows control electronics 130 to determine whether a blister sleeve 140 is properly housed in its respective slot 112, as well as to unlock and partially eject respective blister sleeve 140 from body 110. For instance, spring-loaded lock 150 may include a spring-mounted contact 152 that is depressed and completes a circuit when blister sleeve 140 is fully inserted into its slot 112 and compresses spring 154.

Referring to FIG. 1E, which generally corresponds to the location labeled "1E" in FIG. 1D, a sensor 160 determines whether blister sleeve 140 is in contact therewith. In this embodiment, sensor 160 is operably connected to, and controlled by, electronics 130. Sensor 160 may be instructed by electronics 130 to cause light 118 to blink when it is time to take a medication stored in associated blister sleeve 140. Sensor 160 may provide a signal to electronics 130 indicating whether associated blister sleeve 140 is present and may be used by electronics 130 to determine whether blister sleeve 140 has been removed and then replaced again at dosing time.

In some embodiments, sensor 160 may indicate the placement of a blister sleeve 140 in a respective compartment to electronics 130, provide an alert (e.g., via lights 118) at dosing time, indicate the removal of blister sleeve 140 to electronics 130, and then confirm the correct replacement of blister sleeve 140 to electronics 130 after the medication is taken. Lights 118 may be associated with each compartment in some embodiments. Sound may also be provided in some embodiments. In certain embodiments, one or more lights 119 (see FIG. 1D) within each compartment flash or glow when respective blister sleeve 140 is properly replaced. This may allow the missing blister to be identified by light-sensitive components in some embodiments. See FIGS. 1K and 1L. In certain embodiments, blister sleeve 140 can only be inserted with blisters 172 facing away from the light-sensitive components.

Figure 1G:
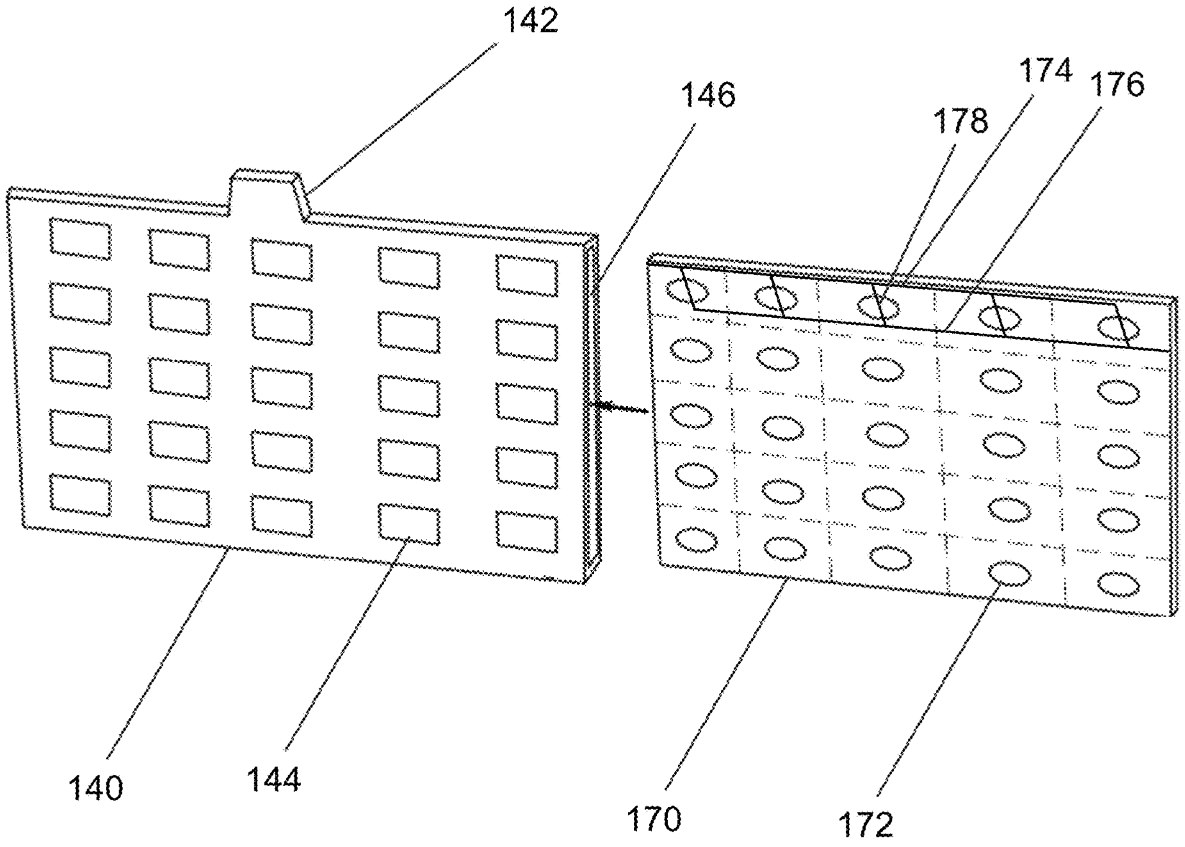
FIG. 1G is a perspective view illustrating the blister sleeve and the blister card shown separately, according to an embodiment of the present invention.

Referring to FIGS. 1F and 1G, openings 144 of blister sleeve 140 expose respective blisters 172 of blister card 170. Blister card 170 also includes wires, with either an individual wire for each blister 172 or connected in parallel, for example. For illustration purposes, only the wires for the top row of blisters are shown. Also, the number of wires at each location would be understood by one skilled in the art. For instance, upper portion 174 would start as a bundle of 5 wires on the left and reduce by one wire per blister until the last wire crosses over the rightmost blister. Similarly, lower portion 176 would start as a single wire on the left and increase by one wire per blister until it reaches 5 wires after the last wire crosses over the rightmost blister. Blister portion 178 of each wire crosses the respective blister and is broken when the medication is removed from that blister.

In some embodiments, blister sleeve 140, blister card 170, and the conduction wires are constructed as one unit. This may eliminate manual alignment of blister cards 170 into blister sleeves 140. Also, the conduction wires may render provision of a light sensing board unnecessary.

Blister card 170 is inserted into a cavity within blister sleeve 140 via a blister card opening 146. In some embodiments, at least one surface of blister sleeve 140 may be transparent or at least semi-transparent so that text and markings on blister card 170 are visible through blister sleeve 140. Thus, blister sleeve 140 provides a hollow shell in which blister card 170 is located when loaded. In some embodiments, blister sleeve 140 may have markings identifying rows and columns to indicate when a medication of a specific blister 172 is used. For instance, rows and columns may be marked to permit the identification of each blister 172. Some medication regiments may require specific pill(s) in blister pack 170 to be consumed at a certain time (e.g., every other day at bedtime). The identification of appropriate blister 172 may provide important confirmation for a clinician. For example, clonazepam may be placed in row four, column three of each blister card. Blister card 170 may have an associated barcode, QR code, serial number, or other unique identifier so that card and its associated medication may be uniquely identified.

Figure 1H:
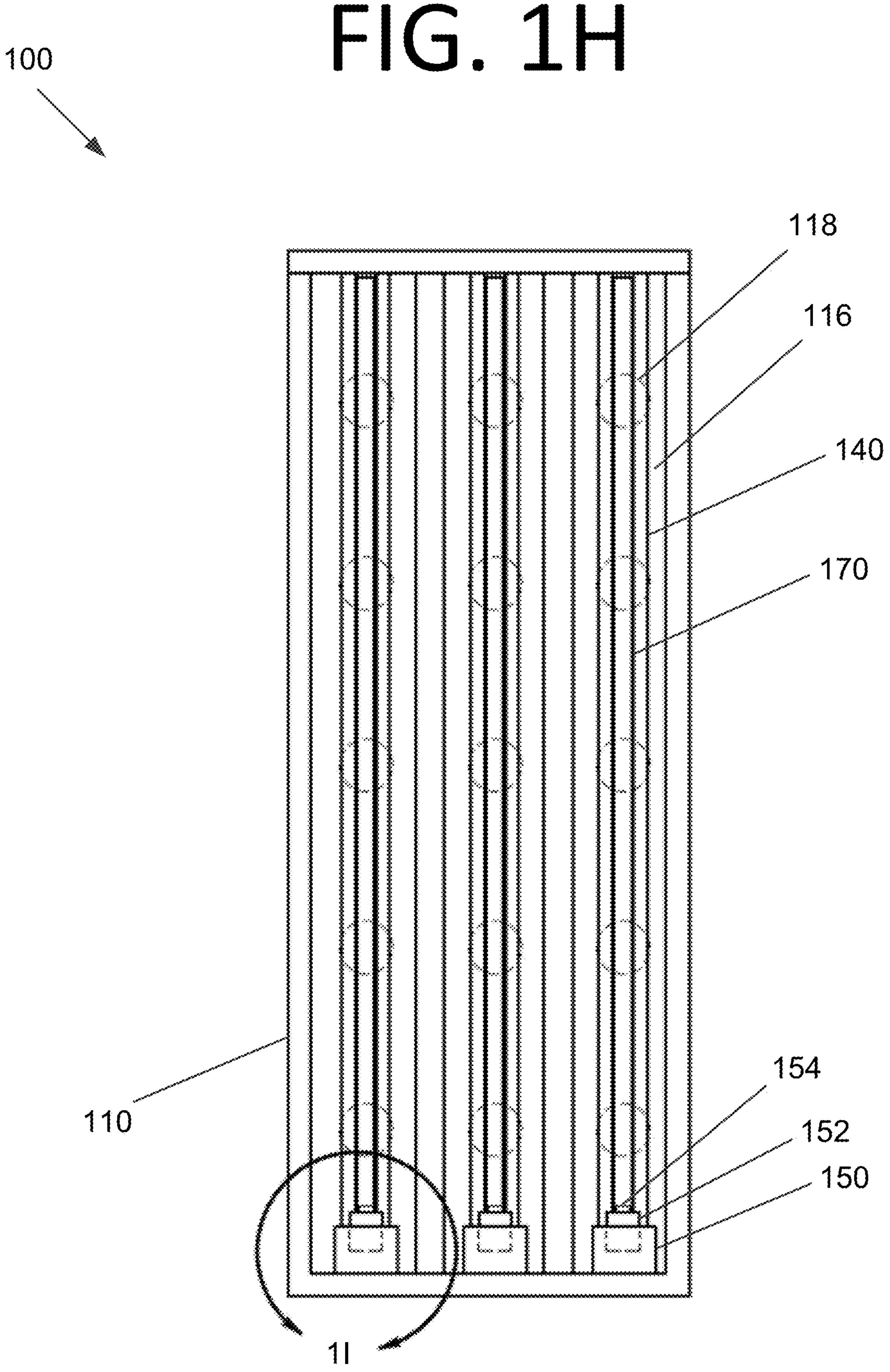
FIG. 1H is a side view illustrating the medication magazine, according to an embodiment of the present invention.
Figure 1I:
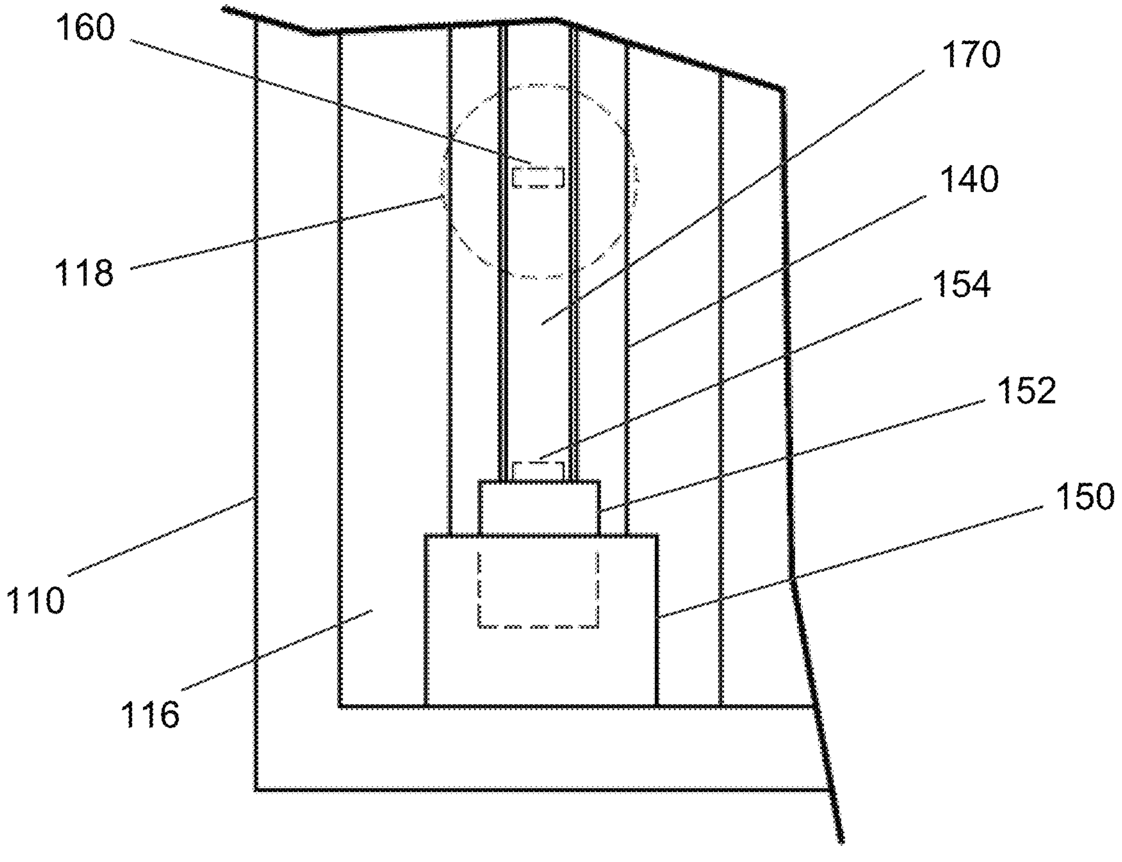
FIG. 1I is a side view illustrating another portion of the medication magazine, according to an embodiment of the present invention.

Referring to FIG. 1H, a side view of blister sleeves 140 and respective blister cards 170 loaded into body 110 of medication magazine 100 is shown. Referring to FIG. 1I, which generally corresponds to the location labeled "II" in FIG. 1H, an enlarged view is shown. Blister sleeve 140 is locked in place within body 110.

Figure 1J:
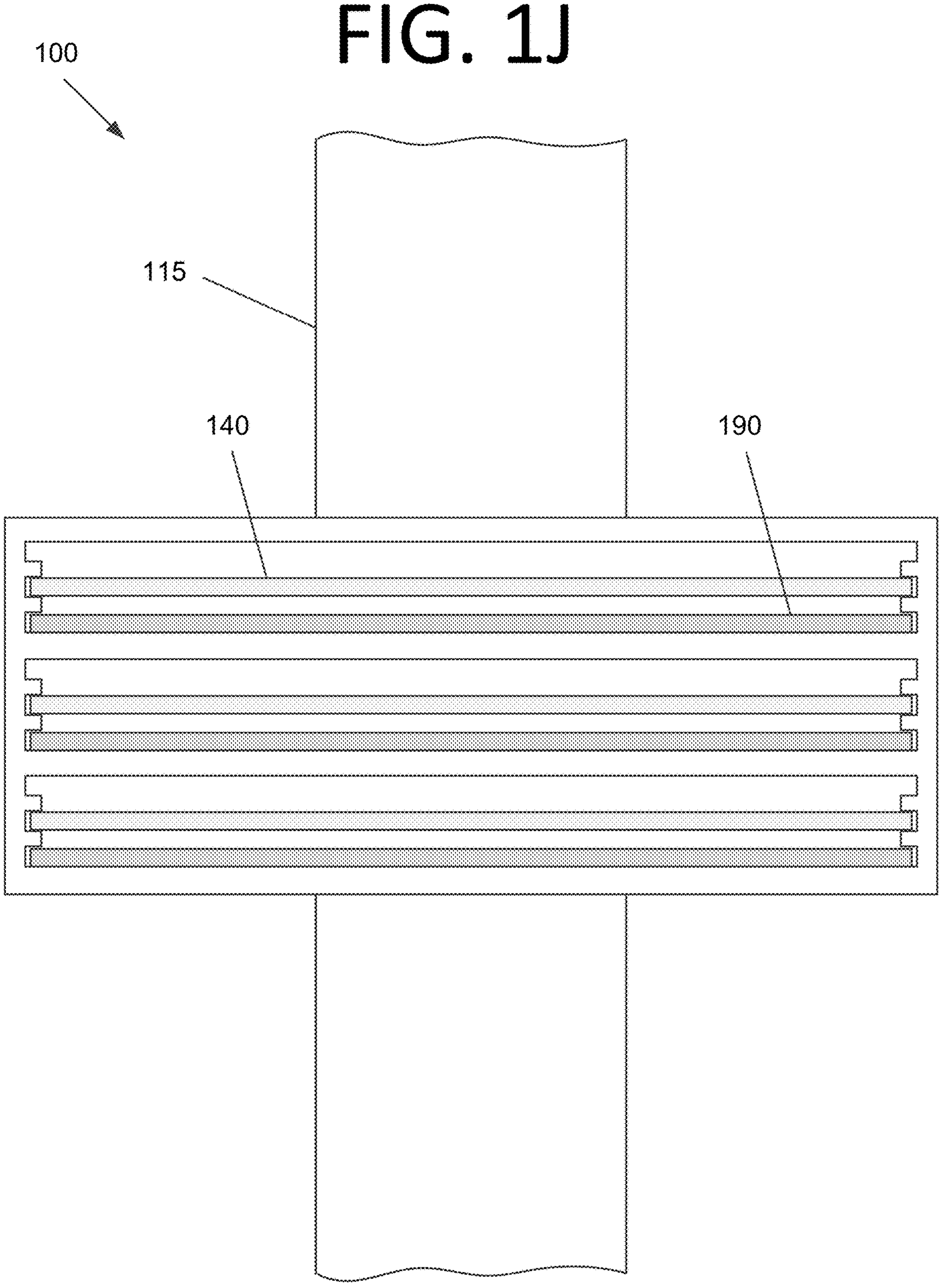
FIG. 1J is a top view illustrating the medication magazine, according to an embodiment of the present invention.
Figure 1K:
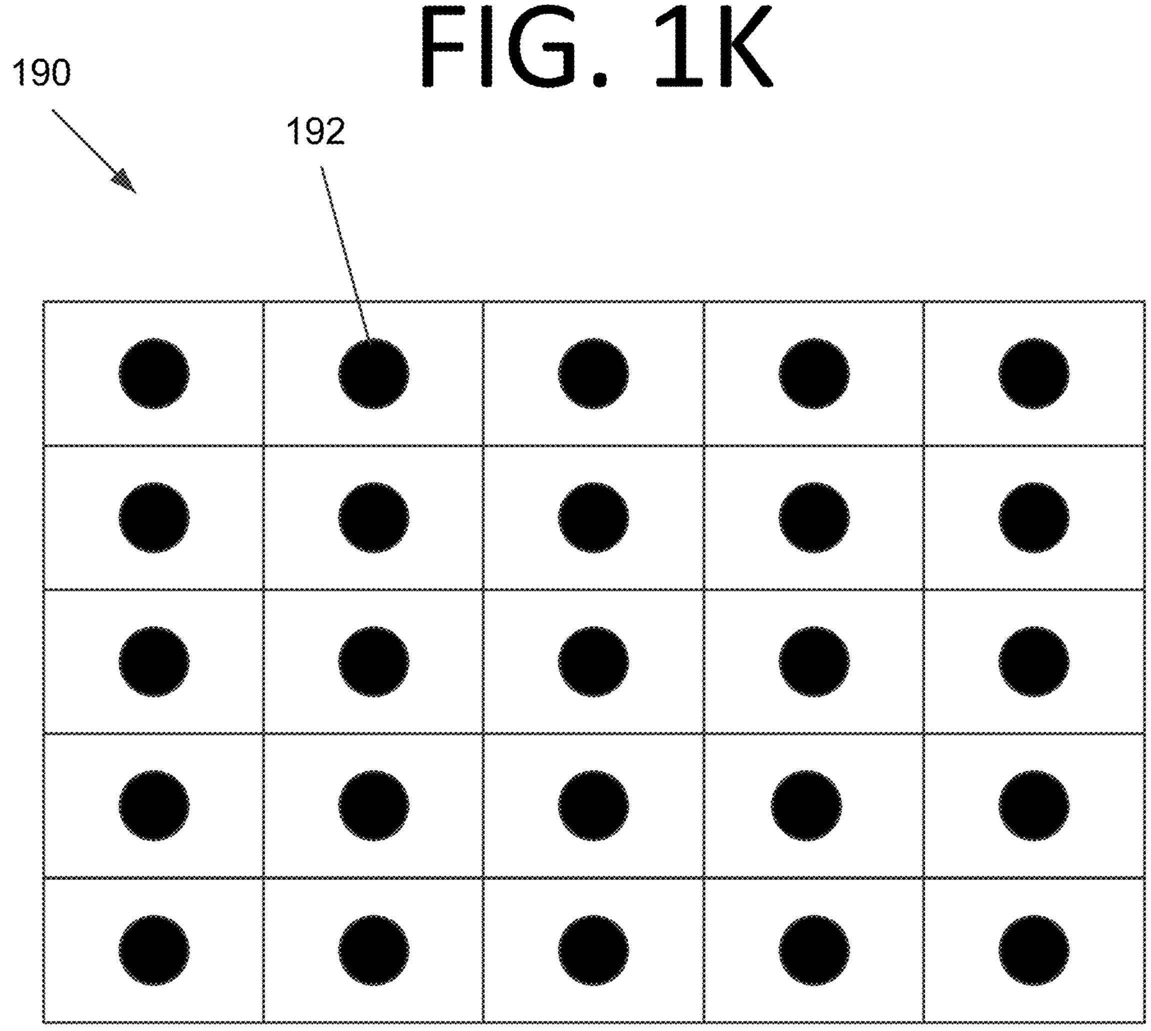
FIG. 1K is a side view illustrating a light-sensitive card, according to an embodiment of the present invention.
Figure 1L:
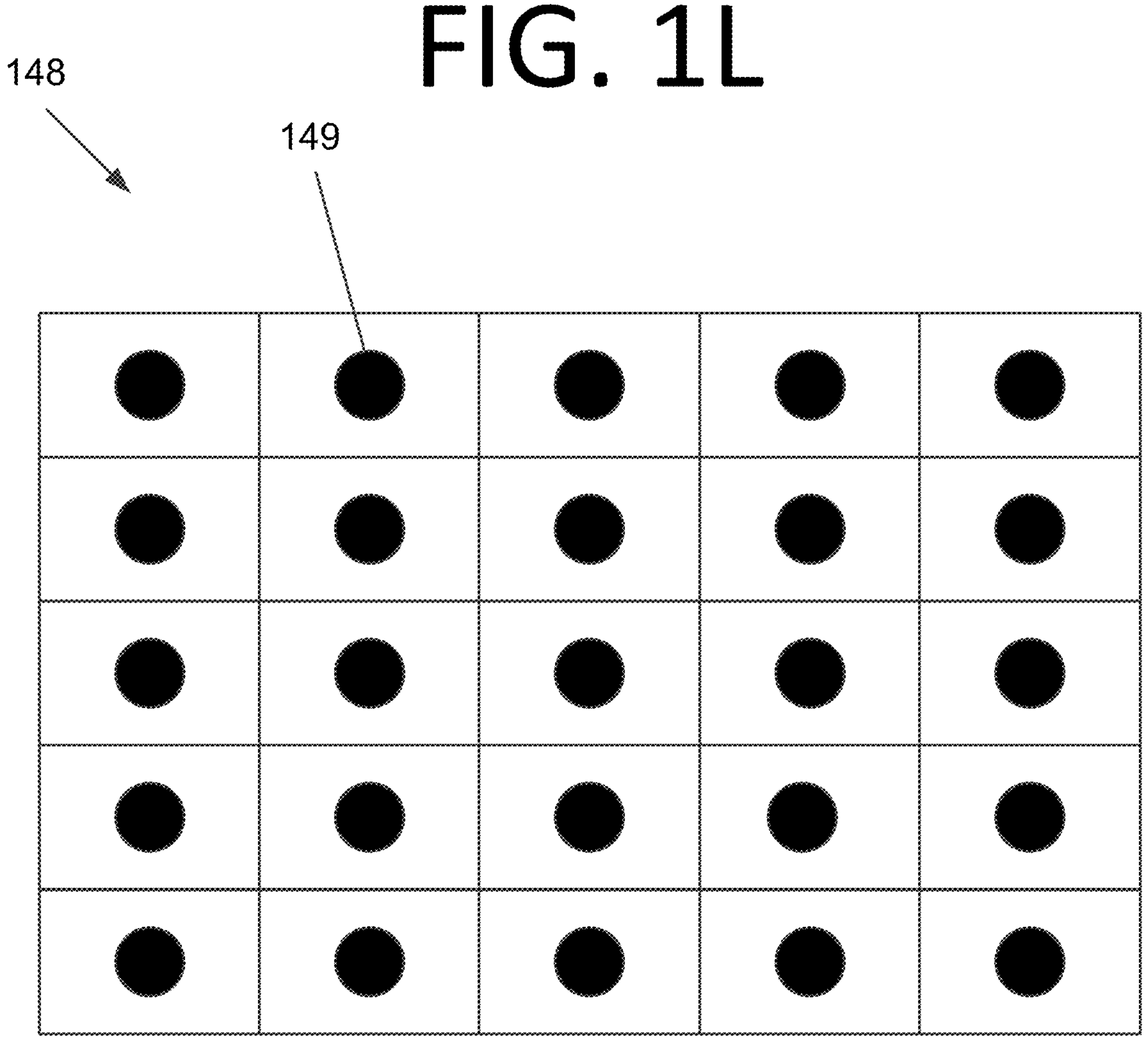
FIG. 1L is a side view illustrating an interior rear surface of a blister sleeve, according to an embodiment of the present invention.

Light-sensitive cards 190 may be included within each compartment of body 110 in some embodiments. See FIGS. 1J and 1K. Light-sensitive cards 190 are operably connected to electronics 130 and include light sensors 192 (e.g., a light-sensitive diode) that are positioned based on locations of blisters 172. The interior of each compartment may be illuminated and the rear side of blister sleeves 140 may be transparent, translucent, or have openings corresponding to the locations of blisters 172 such that light can pass through blisters 172 if they are opened and the packaging material is clear or translucent. This allows light sensors 192 to receive light when a given blister has been opened, indicating that the respective pill has been taken. An attachment mechanism 115, such as a belt, a holster, a clip, etc., may also be provided to make the device wearable. Patients may also place medication magazine in their pocket or purse in some embodiments.

Blister sleeves 140 themselves may include light-sensing components in some embodiments. For instance, in FIG. 1L, an interior rear surface 148 of a blister sleeve 140 is shown. Like light-sensitive card 190, interior rear surface 148 includes light sensors 149. However, in this case, light sensors 149 are inside blister sleeve 140. If blisters 172 include clear or translucent packaging material, then a blister is opened, corresponding light sensor 149 receives light therethrough and provides a signal indicating to electronics 130 that the respective pill has been taken. In some embodiments, in order to save power, light-sensitive card 190 or blister sleeve 140 may switch off when blister sleeve 140 is released from magazine 100. Light-sensitive card 190 or blister sleeve 140 may switch on briefly when blister sleeve 140 is inserted into a respective compartment of body 110 to confirm opened blister(s) 172.

Figure 2:
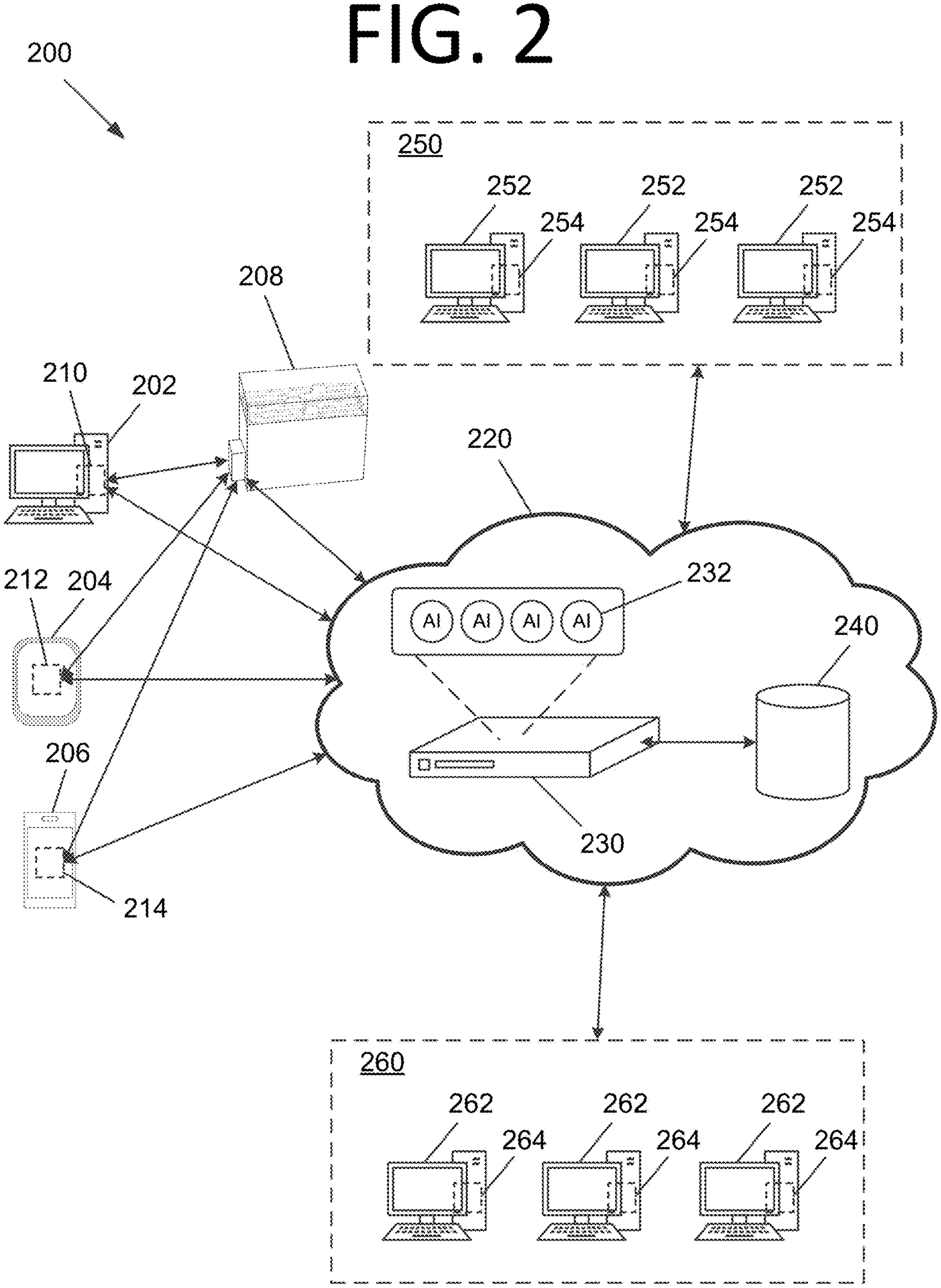
FIG. 2 is an architectural diagram illustrating an intelligent medication management system, according to an embodiment of the present invention.

Per the above, in some embodiments, a medication management system is provided. FIG. 2 is an architectural diagram illustrating an intelligent medication management system 200, according to an embodiment of the present invention.

Intelligent medication management system 200 includes user (e.g., a patient or a care provider) computing systems, such as desktop computer 202, tablet 204, and smart phone 206. However, any desired user computing system may be used without deviating from the scope of the invention including, but not limited to, smart watches, laptop computers, servers, IoT devices, etc. Also, while three user computing systems are shown in FIG. 2, any suitable number of user computing systems may be used without deviating from the scope of the invention. For instance, in some embodiments, dozens, hundreds, thousands, or millions of user computing systems may be used. A medication magazine 208 is also shown and may be the same as or similar to medication magazine 100 of FIGS. 1A-L in some embodiments. Similarly, in some embodiments, dozens, hundreds, thousands, or millions of medication magazines may be used.

Each user computing system 202, 204, 206 has respective medication management processes 210, 212, 214 running thereon. Medication management process(es) 210, 212, 214 may include, but are not limited to, robotic process automation (RPA) robots, part of an operating system, downloadable application(s) for the respective computing system, any other suitable software and/or hardware, or any combination of these without deviating from the scope of the invention. Medication magazine 208 includes electronics that control its operation. In some embodiments the electronics are the same as or similar to electronics 130 of medication magazine 100 of FIGS. 1A-L.

Medication management processes 210, 212, 214 allow users of computing systems 202, 204, 206, respectively, to manage and interact with medication magazine 208. For instance, medication management processes 210, 212, 214 may alert respective users of dosing times, allow users to change dosing schedules, link blister cards to medication magazine 208, authenticate the user to unlock blister sleeves, provide communications to and receive communications from medication magazine 208, etc.

In this embodiment, medication management processes 210, 212, 214 and medication magazine 208 send data to a cloud-based system via a network 220 (e.g., a local area network (LAN), a mobile communications network, a satellite communications network, the Internet, any combination thereof, etc.). The data may include, but is not limited to, what time a dose of a medication was taken, an identification of the associated medication, the dosage of the medication, whether a change of a dosage of a medication occurred and what the new dosage is, whether prescribed medications were changed and which medications the prescription(s) were changed to, whether a given medication was discontinued, patient information (e.g., heart rate, blood pressure, weight, age, etc.), the prescriber's name, the name of the nurse (if present), a visual observation report from a medical professional, any combination thereof, and/or any other suitable information without deviating from the scope of the invention. One or more servers, such as server 230, receive and store data from processes 210, 212, 214 and/or medication magazine 208 in a database, such as database 240.

It should be noted that while one server 230 is shown for illustration purposes, multiple or many servers that are proximate to one another or in a distributed architecture may be employed without deviating from the scope of the invention. In some embodiments, server 230 and database 240 may incorporate or be part of a public cloud architecture, a private cloud architecture, a hybrid cloud architecture, etc. In certain embodiments, server 230 may host multiple software-based servers. In some embodiments, one or more servers, such as server 230, may be implemented via one or more virtual machines (VMs).

In some embodiments, server 230 may call one or more AI/ML models 232 deployed on or otherwise accessible by server 230. AI/ML models 232 may be trained for any suitable purpose without deviating from the scope of the invention, as will be discussed in more detail later herein. For instance, AI/ML models 232 may analyze data provided by processes 210, 212, 214 and/or medication magazine 208 to identify trends and correlations. For instance, AI/ML models 232 may consume vital sign and medication dosage information and recommend a more ideal dosage for a given vital statistic, such a recommending a dosage that appears to provide the most optimal reduction in blood pressure.

Two or more of AI/ML models 232 may be chained in some embodiments (e.g., in series, in parallel, or a combination thereof) such that they collectively provide collaborative output(s). Any desired number and/or type(s) of AI/ML models in any desired configuration may be used without deviating from the scope of the invention. Using multiple AI/ML models may allow the system to develop a global picture of what is happening with respect to a given medication and its dosage(s), for example. Patterns may be determined individually by an AI/ML model or collectively by multiple AI/ML models. In certain embodiments, one or more AI/ML models are deployed locally on at least one of computing systems 202, 204, 206.

Per the above, in some embodiments, multiple AI/ML models 232 may be used. Each AI/ML model 232 is an algorithm (or model) that runs on the data, and the AI/ML model itself may be a deep learning neural network (DLNN) of trained artificial "neurons" that are trained on training data, for example. In some embodiments, AI/ML models 232 may have multiple layers that perform various functions, such as statistical modeling (e.g., hidden Markov models (HMMs)), and utilize deep learning techniques (e.g., long short term memory (LSTM) deep learning, encoding of previous hidden states, etc.) to perform the desired functionality.

Information obtained by server 230 and stored in database 240 may be accessed by data scientists of a healthcare analytics company 250 via computing systems 252 running analytics applications 254. For instance, data scientists may review data that has been obtained from user computing systems and medication magazines, track, measure, and manage the performance of deployed AI/ML models 232, and provide corrections for incorrect predictions by AI/ML models 232. Data scientists may also initiate retraining of AI/ML models 232 once a sufficient number of positive and negative training examples have been received, after a predetermined amount of time, on demand, etc.

A healthcare provider facility 260 may also be able to access the data. For instance, healthcare staff may view patient data, adjust prescriptions, ensure compliance with dosing regimens, etc. via patient care applications 264 running on computing systems 262. This may provide healthcare staff with valuable insights across a healthcare organization.

Figure 3:
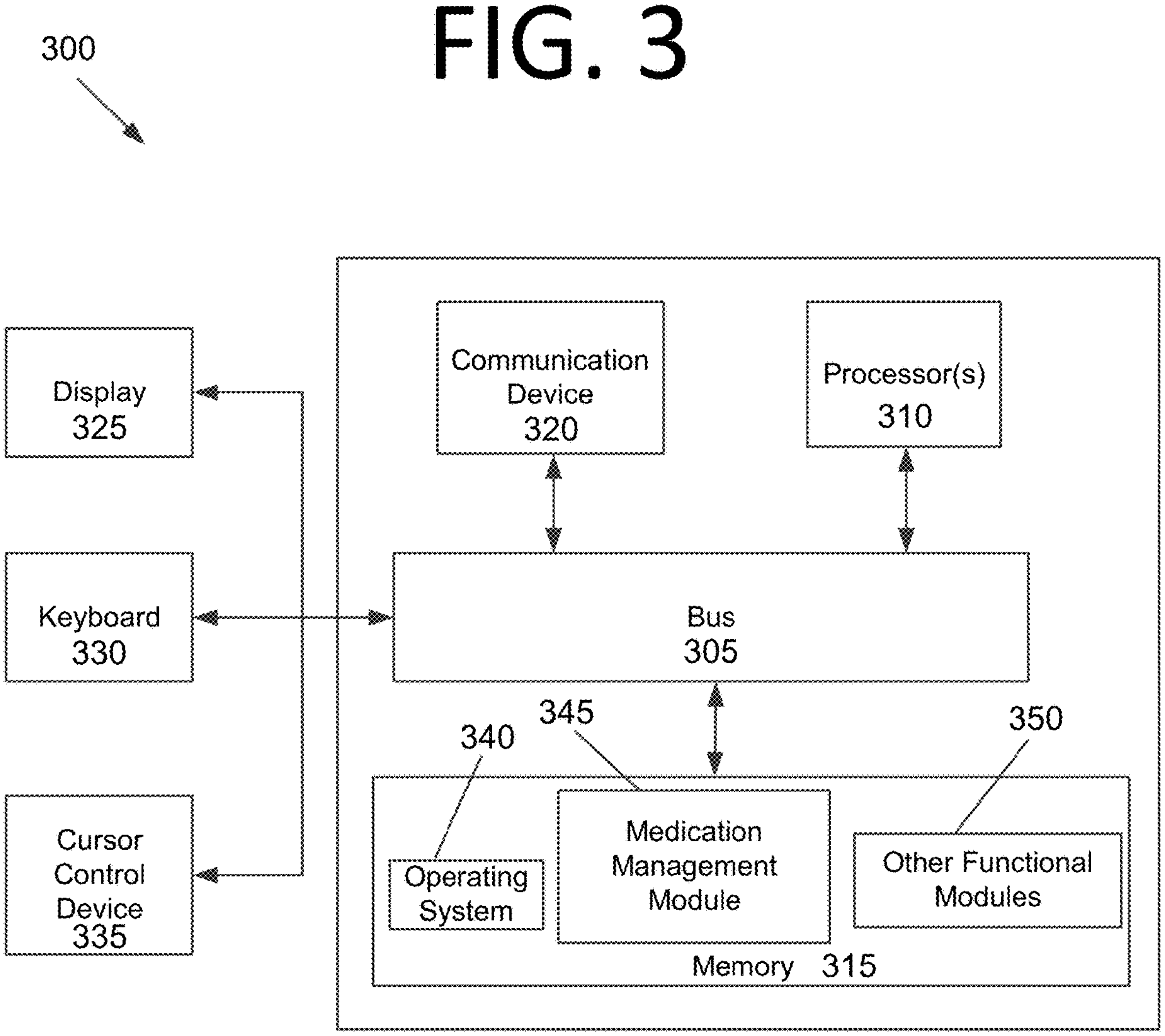
FIG. 3 is an architectural diagram illustrating a computing system configured to provide medication management services, according to an embodiment of the present invention.

FIG. 3 is an architectural diagram illustrating a computing system 300 configured to provide medication management services, according to an embodiment of the present invention. In some embodiments, computing system 300 may be one or more of the computing systems depicted and/or described herein. In certain embodiments, computing system 300 may be part of intelligent medication management system 200 of FIG. 2, such as computing system 202, 204, 206, 252, 262 or server 230.

Computing system 300 includes a bus 305 or other communication mechanism for communicating information, and processor(s) 310 coupled to bus 305 for processing information. Processor(s) 310 may be any type of general or specific purpose processor, including a Central Processing Unit (CPU), an Application Specific Integrated Circuit (ASIC), a Field Programmable Gate Array (FPGA), a Graphics Processing Unit (GPU), multiple instances thereof, and/or any combination thereof. Processor(s) 310 may also have multiple processing cores, and at least some of the cores may be configured to perform specific functions. Multi-parallel processing may be used in some embodiments. In certain embodiments, at least one of processor(s) 310 may be a neuromorphic circuit that includes processing elements that mimic biological neurons. In some embodiments, neuromorphic circuits may not require the typical components of a Von Neumann computing architecture.

Computing system 300 further includes a memory 315 for storing information and instructions to be executed by processor(s) 310. Memory 315 can be comprised of any combination of random access memory (RAM), read-only memory (ROM), flash memory, cache, static storage such as a magnetic or optical disk, or any other types of non-transitory computer-readable media or combinations thereof. Non-transitory computer-readable media may be any available media that can be accessed by processor(s) 310 and may include volatile media, non-volatile media, or both. The media may also be removable, non-removable, or both. Computing system 300 includes a communication device 320, such as a transceiver, to provide access to a communications network via a wireless and/or wired connection. In some embodiments, communication device 320 may include one or more antennas that are singular, arrayed, phased, switched, beamforming, beamsteering, a combination thereof, and/or any other antenna configuration without deviating from the scope of the invention. Processor(s) 310 are further coupled via bus 305 to a display 325. Any suitable display device and haptic I/O may be used without deviating from the scope of the invention.

A keyboard 330 and a cursor control device 335, such as a computer mouse, a touchpad, etc., are further coupled to bus 305 to enable a user to interface with computing system 300. However, in certain embodiments, a physical keyboard and mouse may not be present, and the user may interact with the device solely through display 325 and/or a touchpad (not shown). Any type and combination of input devices may be used as a matter of design choice. In certain embodiments, no physical input device and/or display is present. For instance, the user may interact with computing system 300 remotely via another computing system in communication therewith, or computing system 300 may operate autonomously.

Memory 315 stores software modules that provide functionality when executed by processor(s) 310. The modules include an operating system 340 for computing system 300. The modules further include a medication management module 345 that is configured to perform all or part of the processes described herein or derivatives thereof. Computing system 300 may include one or more additional functional modules 350 that include additional functionality.

One skilled in the art will appreciate that a "computing system" could be embodied as a server, an embedded computing system, a personal computer, a console, a personal digital assistant (PDA), a cell phone, a tablet computing device, a quantum computing system, or any other suitable computing device, or combination of devices without deviating from the scope of the invention. Presenting the above-described functions as being performed by a "system" is not intended to limit the scope of the present invention in any way, but is intended to provide one example of the many embodiments of the present invention. Indeed, methods, systems, and apparatuses disclosed herein may be implemented in localized and distributed forms consistent with computing technology, including cloud computing systems. The computing system could be part of or otherwise accessible by a local area network (LAN), a mobile communications network, a satellite communications network, the Internet, a public or private cloud, a hybrid cloud, a server farm, any combination thereof, etc. Any localized or distributed architecture may be used without deviating from the scope of the invention.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, include one or more physical or logical blocks of computer instructions that may, for instance, be organized as an object, procedure, or function. Nevertheless, the executables of an identified module need not be physically located together, but may include disparate instructions stored in different locations that, when joined logically together, comprise the module and achieve the stated purpose for the module. Further, modules may be stored on a computer-readable medium, which may be, for instance, a hard disk drive, flash device, RAM, tape, and/or any other such non-transitory computer-readable medium used to store data without deviating from the scope of the invention.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Figure 4A:
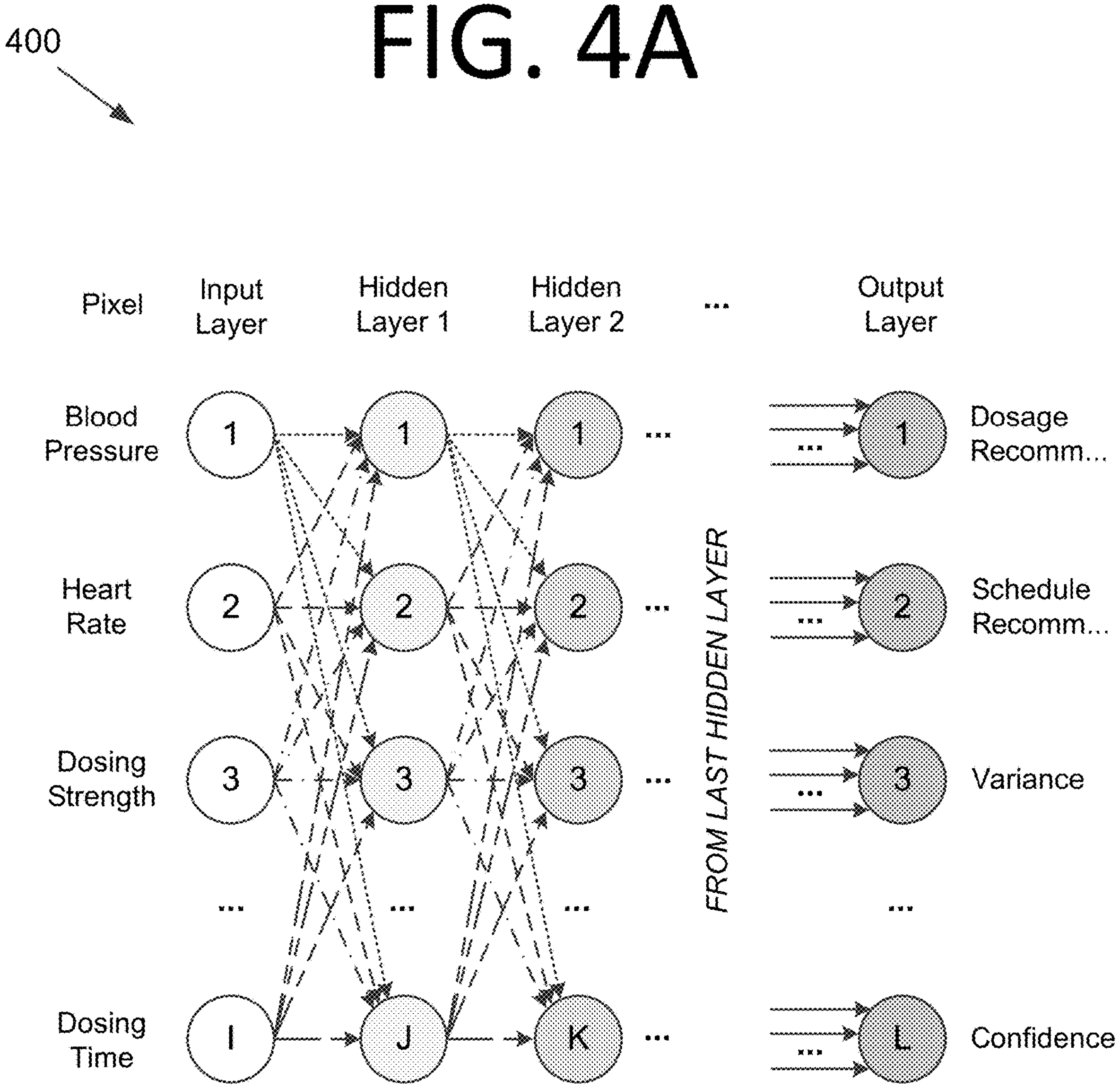
FIG. 4A illustrates an example of a neural network that has been trained to recognize trends in patient data, according to an embodiment of the present invention.

Various types of AI/ML models may be trained and deployed without deviating from the scope of the invention. For instance, FIG. 4A illustrates an example of a neural network 400 that has been trained to recognize trends in patient data, according to an embodiment of the present invention. Here, neural network 400 receives blood pressure, heart rate, dosing strength, dosing time, and other desired inputs as input for input "neurons" 1 to I of the input layer. In this case, I is the number of inputs.

Neural network 400 also includes a number of hidden layers. Both DLNNs and shallow learning neural networks (SLNNs) usually have multiple layers, although SLNNs may only have one or two layers in some cases, and normally fewer than DLNNs. Typically, the neural network architecture includes an input layer, multiple intermediate layers, and an output layer, as is the case in neural network 400.

A DLNN often has many layers (e.g., 10, 50, 200, etc.) and subsequent layers typically reuse features from previous layers to compute more complex, general functions. A SLNN, on the other hand, tends to have only a few layers and train relatively quickly since expert features are created from raw data samples in advance. However, feature extraction is laborious. DLNNs, on the other hand, usually do not require expert features, but tend to take longer to train and have more layers.

For both approaches, the layers are trained simultaneously on the training set, normally checking for overfitting on an isolated cross-validation set. Both techniques can yield excellent results, and there is considerable enthusiasm for both approaches. The optimal size, shape, and quantity of individual layers varies depending on the problem that is addressed by the respective neural network.

Returning to FIG. 4A, inputs from the input layer are fed as inputs to the J neurons of hidden layer 1. While all inputs are fed to each neuron in this example, various architectures are possible that may be used individually or in combination including, but not limited to, feed forward networks, radial basis networks, deep feed forward networks, deep convolutional inverse graphics networks, convolutional neural networks, recurrent neural networks, artificial neural networks, long/short term memory networks, gated recurrent unit networks, generative adversarial networks, liquid state machines, auto encoders, variational auto encoders, denoising auto encoders, sparse auto encoders, extreme learning machines, echo state networks, Markov chains, Hopfield networks, Boltzmann machines, restricted Boltzmann machines, deep residual networks, Kohonen networks, deep belief networks, deep convolutional networks, support vector machines, neural Turing machines, or any other suitable type or combination of neural networks without deviating from the scope of the invention.

Hidden layer 2 receives inputs from hidden layer 1, hidden layer 3 receives inputs from hidden layer 2, and so on for all hidden layers until the last hidden layer provides its outputs as inputs for the output layer. It should be noted that numbers of neurons I, J, K, and L are not necessarily equal, and thus, any desired number of layers may be used for a given layer of neural network 400 without deviating from the scope of the invention. Indeed, in certain embodiments, the types of neurons in a given layer may not all be the same. Neural network 400 is trained to provide recommendations for dosage and dosing schedule, as well as variance among patients and a confidence score for the recommendations.

It should be noted that neural networks are probabilistic constructs that typically have a confidence score. This may be a score learned by the AI/ML model based on how often a similar input was correctly identified during training. Some common types of confidence scores include a decimal number between 0 and 1 (which can be interpreted as a percentage of confidence), a number between negative co and positive co, or a set of expressions (e.g., "low," "medium," and "high"). Various post-processing calibration techniques may also be employed in an attempt to obtain a more accurate confidence score, such as temperature scaling, batch normalization, weight decay, negative log likelihood (NLL), etc.

"Neurons" in a neural network are mathematical functions that are typically based on the functioning of a biological neuron. Neurons receive weighted input and have a summation and an activation function that governs whether they pass output to the next layer. This activation function may be a nonlinear thresholded activity function where nothing happens if the value is below a threshold, but then the function linearly responds above the threshold (i.e., a rectified linear unit (ReLU) nonlinearity). Summation functions and ReLU functions are used in deep learning since real neurons can have approximately similar activity functions. Via linear transforms, information can be subtracted, added, etc. In essence, neurons act as gating functions that pass output to the next layer as governed by their underlying mathematical function. In some embodiments, different functions may be used for at least some neurons.

Figure 4B:
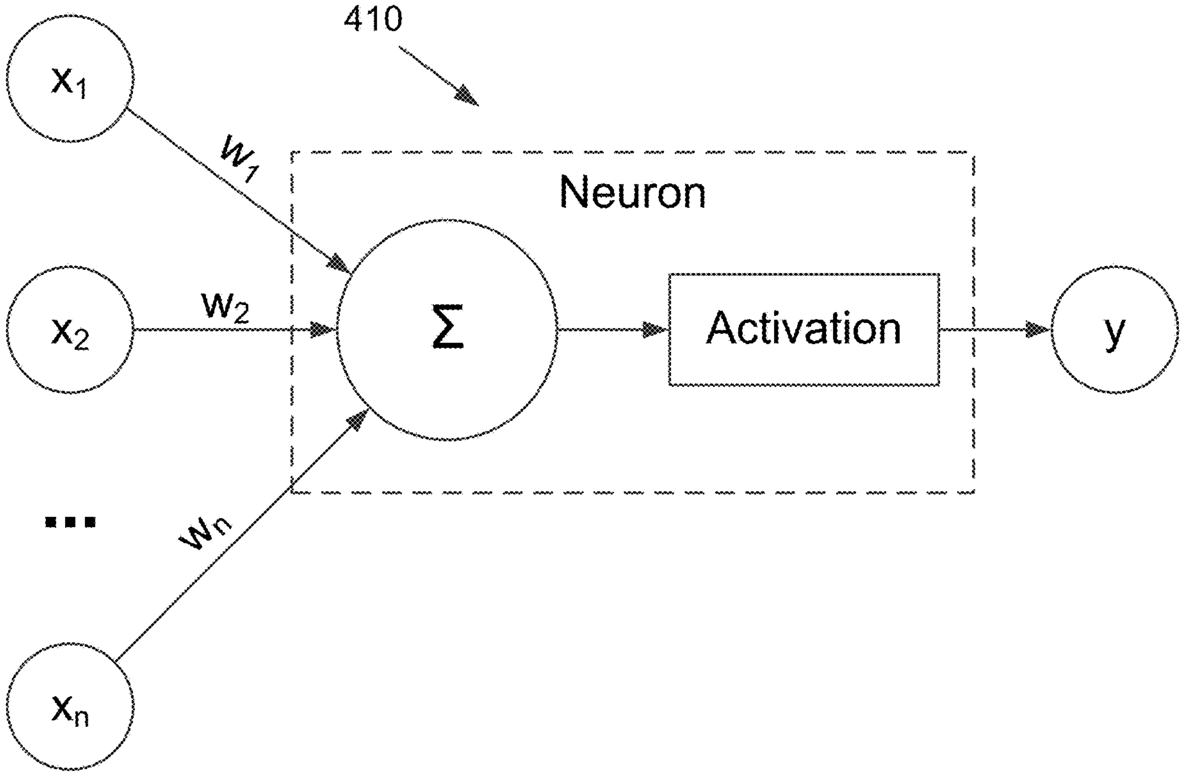
FIG. 4B illustrates an example of a neuron, according to an embodiment of the present invention.

An example of a neuron 410 is shown in FIG. 4B. Inputs $x_1, x_2, \ldots, x_n$ from a preceding layer are assigned respective weights $w_1, w_2, \ldots, w_n$. Thus, the collective input from preceding neuron 1 is $w_1x_1$. These weighted inputs are used for the neuron's summation function modified by a bias, such as:

$$\sum_{i=1}^{m}(w_i x_i) + \text{bias} \tag{1}$$

This summation is compared against an activation function $f(x)$ to determine whether the neuron "fires". For instance, $f(x)$ may be given by:

$$f(x) = \begin{cases} 1 & \text{if } \sum wx + \text{bias} \geq 0 \\ 0 & \text{if } \sum wx + \text{bias} < 0 \end{cases} \tag{2}$$

The output y of neuron 710 may thus be given by:

$$y = f(x)\sum_{i=1}^{m}(w_i x_i) + \text{bias} \tag{3}$$

In this case, neuron 410 is a single-layer perceptron. However, any suitable neuron type or combination of neuron types may be used without deviating from the scope of the invention. It should also be noted that the ranges of values of the weights and/or the output value(s) of the activation function may differ in some embodiments without deviating from the scope of the invention.

The goal, or "reward function" is often employed, such as for this case the successful identification of graphical elements in the image. A reward function explores intermediate transitions and steps with both short-term and long-term rewards to guide the search of a state space and attempt to achieve a goal (e.g., successful recommendation of beneficial dosages and dosing schedules).

During training, various labeled data (in this case, images) are fed through neural network 400. Successful identifications strengthen weights for inputs to neurons, whereas unsuccessful identifications weaken them. A cost function, such as mean square error (MSE) or gradient descent may be used to punish predictions that are slightly wrong much less than predictions that are very wrong. If the performance of the AI/ML model is not improving after a certain number of training iterations, a data scientist may modify the reward function, provide indications of where non-identified graphical elements are, provide corrections of misidentified graphical elements, etc.

Backpropagation is a technique for optimizing synaptic weights in a feedforward neural network. Backpropagation may be used to "pop the hood" on the hidden layers of the neural network to see how much of the loss every node is responsible for, and subsequently updating the weights in such a way that minimizes the loss by giving the nodes with higher error rates lower weights, and vice versa. In other words, backpropagation allows data scientists to repeatedly adjust the weights so as to minimize the difference between actual output and desired output.

The backpropagation algorithm is mathematically founded in optimization theory. In supervised learning, training data with a known output is passed through the neural network and error is computed with a cost function from known target output, which gives the error for backpropagation. Error is computed at the output, and this error is transformed into corrections for network weights that will minimize the error.

In the case of supervised learning, an example of backpropagation is provided below. A column vector input x is processed through a series of N nonlinear activity functions $f_i$ between each layer $i=1, \ldots, N$ of the network, with the output at a given layer first multiplied by a synaptic matrix $W_i$, and with a bias vector $b_i$ added. The network output o, given by $$o = f_N(W_N f_{N-1}(W_{N-1} f_{N-2}(\ldots f_1(W_1 x + b_1)\ldots) + b_{N-1}) + b_N) \tag{4}$$

In some embodiments, o is compared with a target output t, resulting in an error $$E = \frac{1}{2}\|o - t\|^2,$$

which is desired to be minimized.

Optimization in the form of a gradient descent procedure may be used to minimize the error by modifying the synaptic weights $W_i$ for each layer. The gradient descent procedure requires the computation of the output o given an input x corresponding to a known target output t, and producing an error o−t. This global error is then propagated backwards giving local errors for weight updates with computations similar to, but not exactly the same as, those used for forward propagation. In particular, the backpropagation step typically requires an activity function of the form $p_j(n_j)=f_j'(n_j)$, where $n_j$ is the network activity at layer j (i.e., $n_j=W_j o_{j-1}+b_j$) where $o_j=f_j(n_j)$ and the apostrophe ' denotes the derivative of the activity function f.

The weight updates may be computed via the formulae:

$$d_j = \begin{cases} (o - t)\circ p_j(n_j), & j = N \\ W_{j+1}^T d_{j+1} \circ p_j(n_j), & j < N \end{cases} \tag{5}$$

$$\frac{\partial E}{\partial W_{j+1}} = d_{j+1}(o_j)^T \tag{6}$$

$$\frac{\partial E}{\partial b_{j+1}} = d_{j+1} \tag{7}$$

$$W_j^{new} = W_j^{old} - \eta\frac{\partial E}{\partial W_j} \tag{8}$$

$$b_j^{new} = b_j^{old} - \eta\frac{\partial E}{\partial b_j} \tag{9}$$

where ∘ denotes a Hadamard product (i.e., the element-wise product of two vectors), $^T$ denotes the matrix transpose, and $o_j$ denotes $f_j(W_j o_{j-1}+b_j)$, with $o_0=x$. Here, the learning rate η is chosen with respect to machine learning considerations. Below, η is related to the neural Hebbian learning mechanism used in the neural implementation. Note that the synapses W and b can be combined into one large synaptic matrix, where it is assumed that the input vector has appended ones, and extra columns representing the b synapses are subsumed to W.

The AI/ML model may be trained over multiple epochs until it reaches a good level of accuracy (e.g., 97% or better using an F2 or F4 threshold for detection and approximately 2,000 epochs). This accuracy level may be determined in some embodiments using an F1 score, an F2 score, an F4 score, or any other suitable technique without deviating from the scope of the invention. Once trained on the training data, the AI/ML model may be tested on a set of evaluation data that the AI/ML model has not encountered before. This helps to ensure that the AI/ML model is not "over fit" such that it identifies graphical elements in the training data well, but does not generalize well to other images.

In some embodiments, it may not be known what accuracy level is possible for the AI/ML model to achieve. Accordingly, if the accuracy of the AI/ML model is starting to drop when analyzing the evaluation data (i.e., the model is performing well on the training data, but is starting to perform less well on the evaluation data), the AI/ML model may go through more epochs of training on the training data (and/or new training data). In some embodiments, the AI/ML model is only deployed if the accuracy reaches a certain level or if the accuracy of the trained AI/ML model is superior to an existing deployed AI/ML model. In certain embodiments, a collection of trained AI/ML models may be used to accomplish a task.

Figure 5:
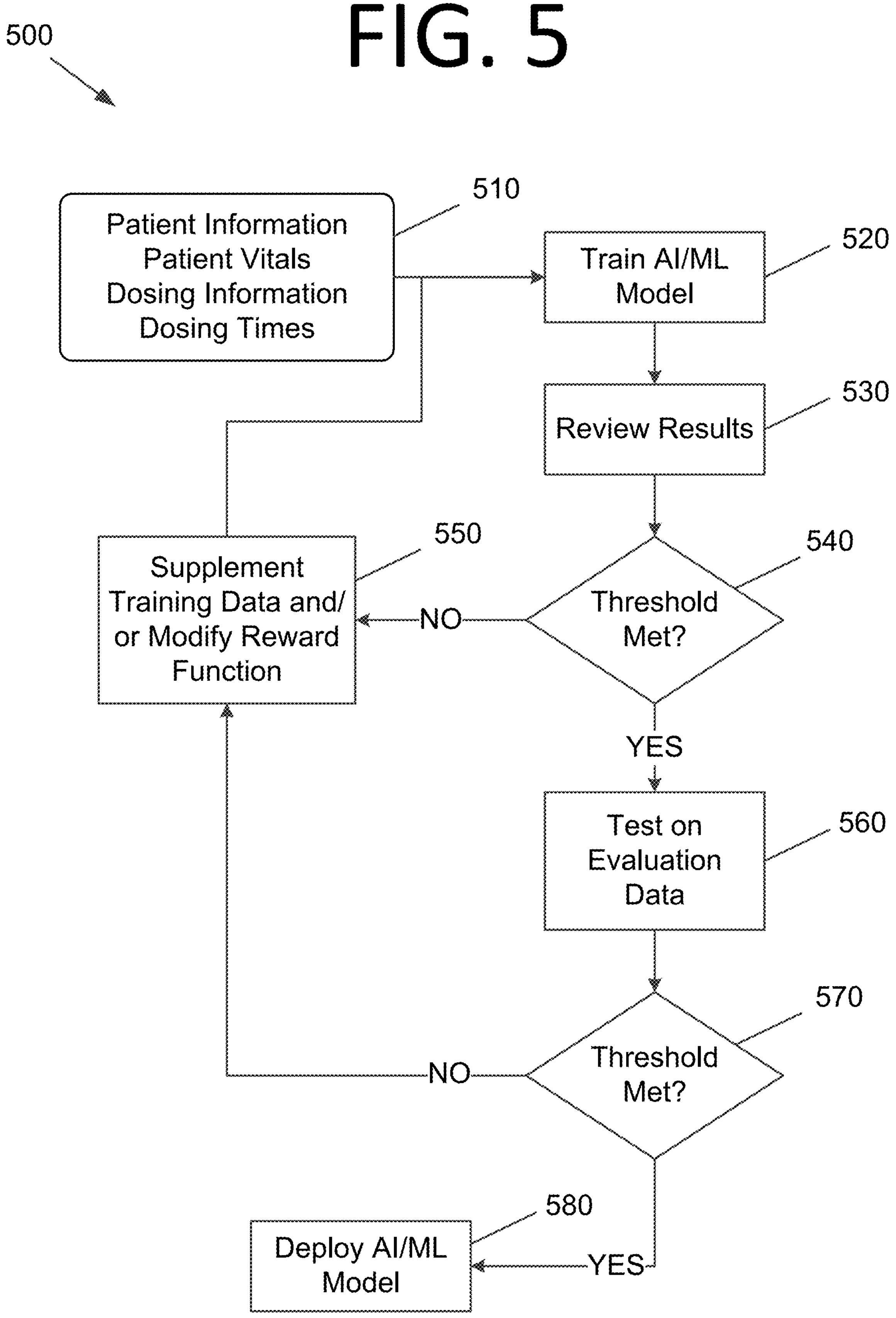
FIG. 5 is a flowchart illustrating a process for training AI/ML model(s), according to an embodiment of the present invention.

FIG. 5 is a flowchart illustrating a process 500 for training AI/ML model(s), according to an embodiment of the present invention. The process begins with providing training data, for instance, patient information, patient vitals, dosing information, and dosing times, at 510. The nature of the training data that is provided will depend on the objective that the AI/ML model is intended to achieve. The AI/ML model is then trained over multiple epochs at 520 and results are reviewed at 530.

If the AI/ML model fails to meet a desired confidence threshold at 540, the training data is supplemented and/or the reward function is modified to help the AI/ML model achieve its objectives better at 550 and the process returns to step 520. If the AI/ML model meets the confidence threshold at 540, the AI/ML model is tested on evaluation data at 560 to ensure that the AI/ML model generalizes well and that the AI/ML model is not over fit with respect to the training data. The evaluation data may include screens, source data, etc. that the AI/ML model has not processed before. If the confidence threshold is met at 570 for the evaluation data, the AI/ML model is deployed at 580. If not, the process returns to step 550 and the AI/ML model is trained further.

Figure 6:
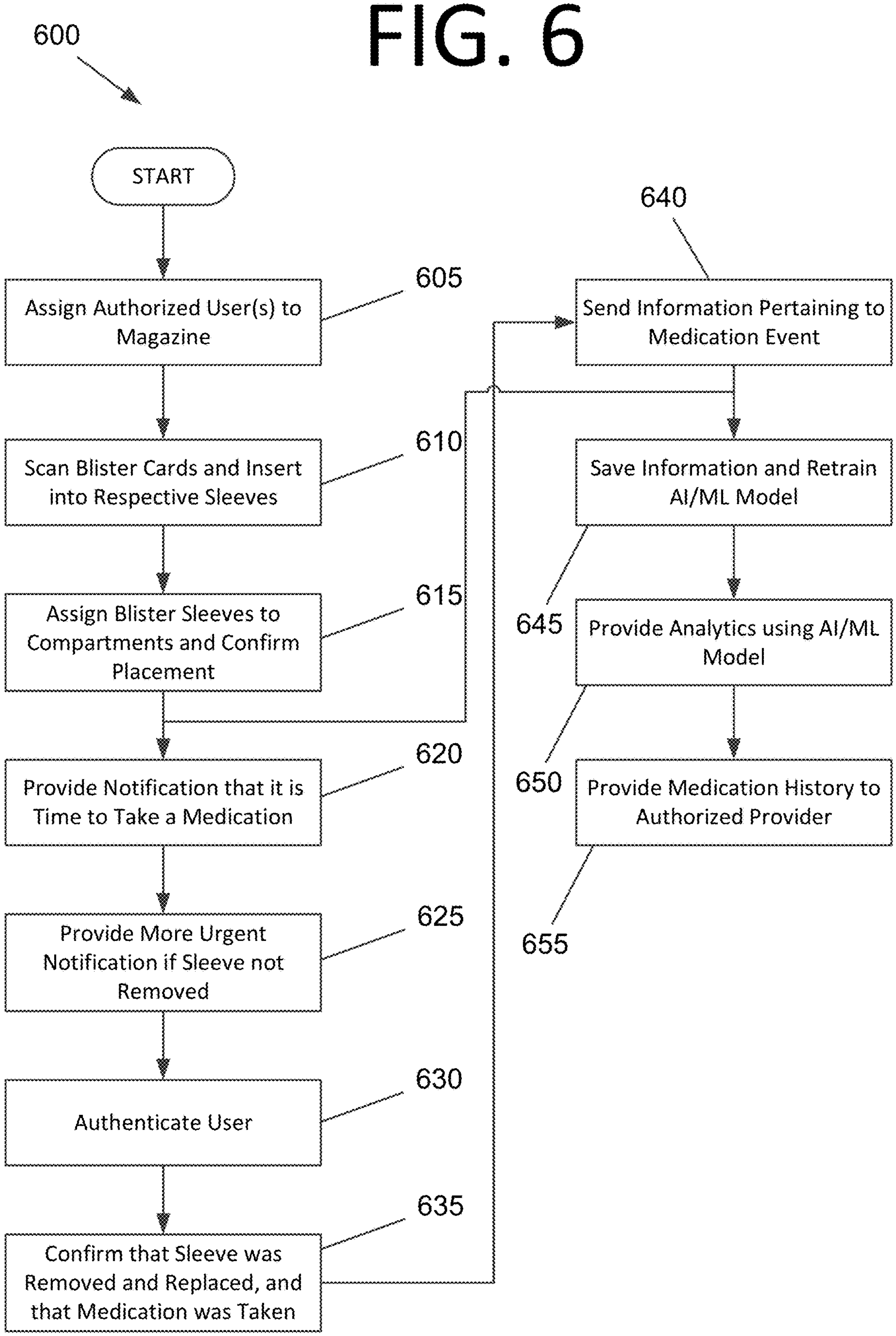
FIG. 6 is a flowchart illustrating a process for medication management, according to an embodiment of the present invention.

FIG. 6 is a flowchart illustrating a process 600 for medication management, according to an embodiment of the present invention. The process begins with assigning authorized user(s) to a medication magazine at 605. An authorized user then scans blister cards and inserts the blister cards at 610 using the medication magazine or an external computing system. The blister sleeves are then assigned to compartments and placement in the compartments is confirmed at 615. When it is time to take a medication, the medication magazine provides a notification at 620, such as via light(s), speaker(s), etc. If an authorized user does not authenticate him or herself after a period of time, a more urgent notification is provided at 625.

The authorized user is authenticated at 630. The medication magazine then confirms that the appropriate medication sleeve(s) were removed and replaced, as well as that the correct mediation dose(s) were taken at 635. If this is not the case, the user may be notified by the medication magazine.

The medication magazine then sends information to an external computing system at 640, such as a laptop or desktop computer, a smart phone, a server that is part of a cloud computing solution, etc. This information may include, but is not limited to, the specific pill(s) in the blister card(s) that were taken, the type of the medication(s), the dosage amount(s), the time that the pill(s) were taken, patient information (e.g., vitals, weight, height, ethnicity, age, etc.), the amount of time that the patient has been on the medication(s), etc. The process of using the medication magazine is then repeated at 620 for the next dosing time.

The information from the medication magazine is saved and used as part of the training data to train or retrain an AI/ML model at 645. Analytics are provided using analytics from the AI/ML model at 650. For instance, the AI/ML model may find trends in the patient information that can be used for more effective dosing schedules and/or dosages. Medication usage information is provided to an authorized provider at 655, such as a doctor, a nurse, etc.

Figure 7:
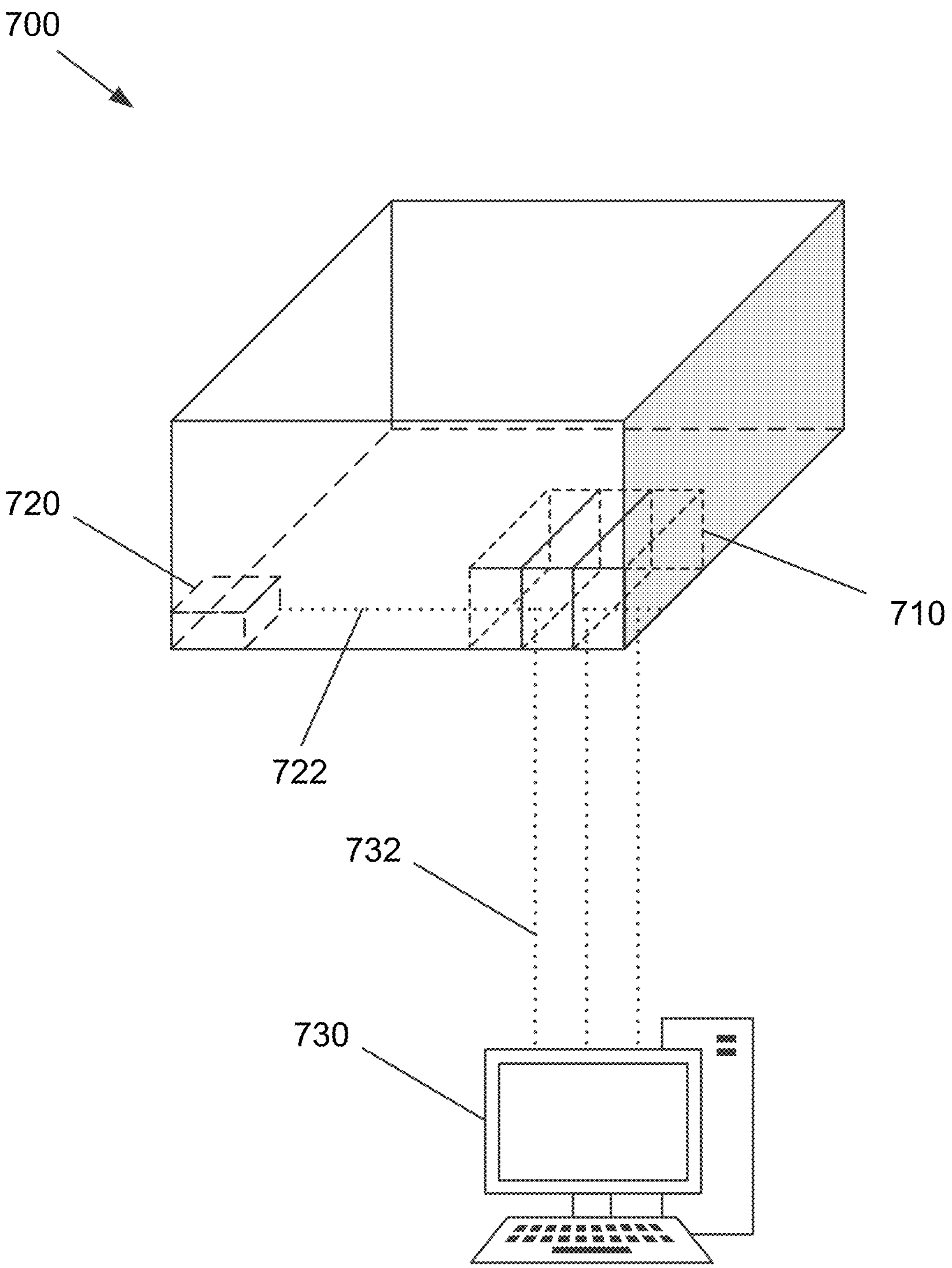
FIG. 7 is a perspective view illustrating an intelligent drawer that holds multiple magazines or blister sleeves, according to an embodiment of the present invention.

FIG. 7 is a perspective view illustrating an intelligent drawer 700, according to an embodiment of the present invention. Intelligent drawer 700 includes multiple magazines or blister sleeves 710 that may include a simpler controller that can convey information to a drawer controller 720 and/or an external computing system 730 (e.g., computing system 300 of FIG. 3) via connections 722, 732, respectively, that are in contact with contact points (not shown) of magazines or blister sleeves 710). In certain embodiments, the connections may be wireless. Similar information to that discussed above with respect to FIGS. 1A-L may be provided in some embodiments. In certain embodiments, drawer controller 720 may be operably connected to a display (not shown) that displays a user interface through which users may interact with intelligent drawer 700 and its contents.

Figure 8:
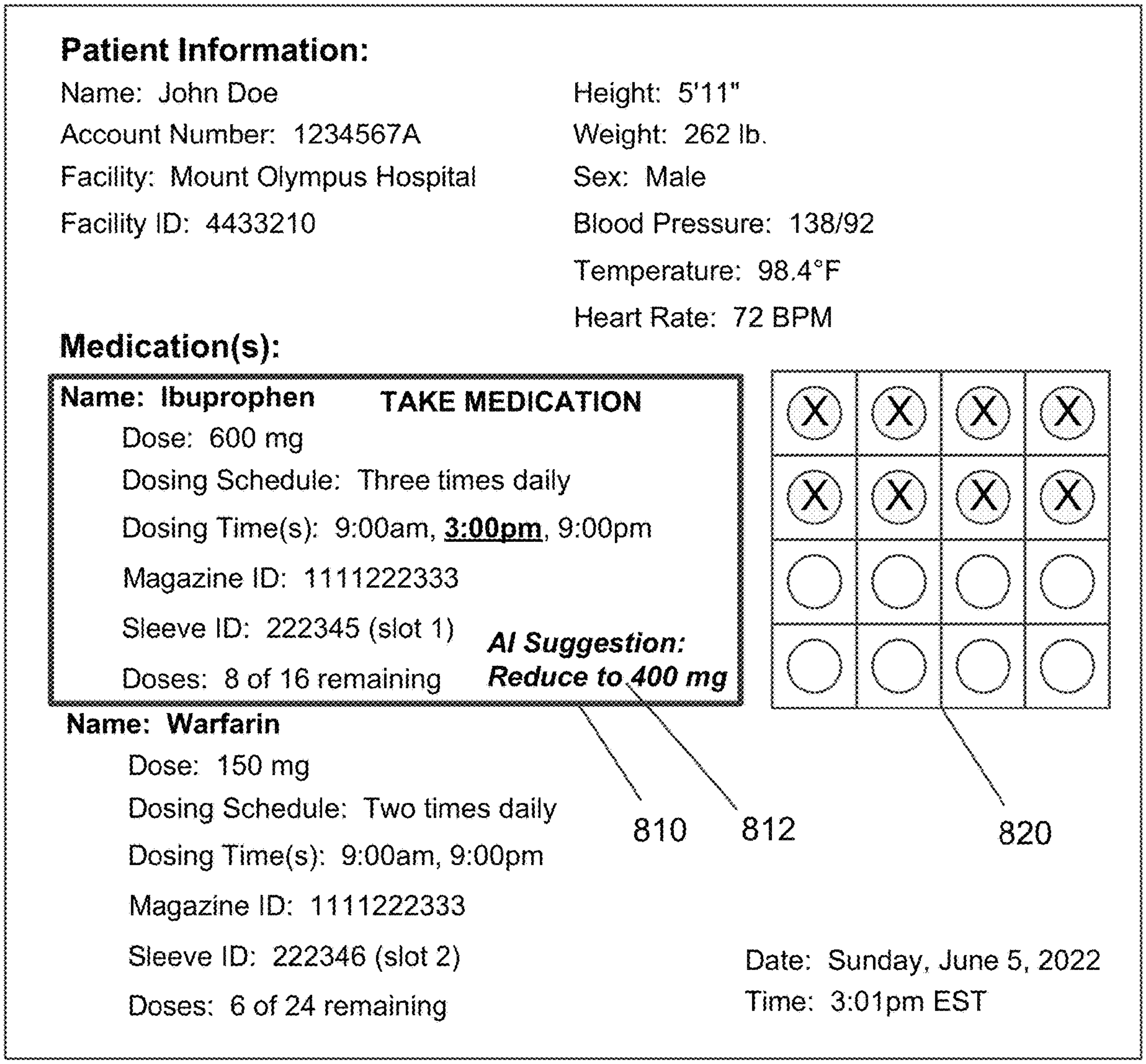
FIG. 8 illustrates a medication management screen, according to an embodiment of the present invention.

FIG. 8 illustrates a medication management interface 800, according to an embodiment of the present invention. In some embodiments, medication management interface 800 may be provided by a computing system, a medication magazine, a blister sleeve, a drawer, or any other suitable device without deviating from the scope of the invention. Medication management interface 800 displays various patient information, such as the patent name, account number, facility, height, weight, sex, blood pressure, temperature, and heart rate. In some embodiments, the user may be able to access a history of certain statistics, such as weight, blood pressure, temperature, and heart rate. This may help the user to see changes in these measurements over time, and potentially changes due to one or more medications.

When it is time to take a medication, this medication is highlighted 810. In some embodiments, if an AI/ML model has analyzed data from multiple patients and determined a new dosage that appears to be more beneficial to one or more targeted statistics (e.g., blood pressure, heart rate, etc.), an AI suggestion 812 may be included. Also, a blister representation 820 visually shows the user which blisters have been used and which still remain in the blister pack. This may be determined via a conduction seal, for example.

Figure 9A:
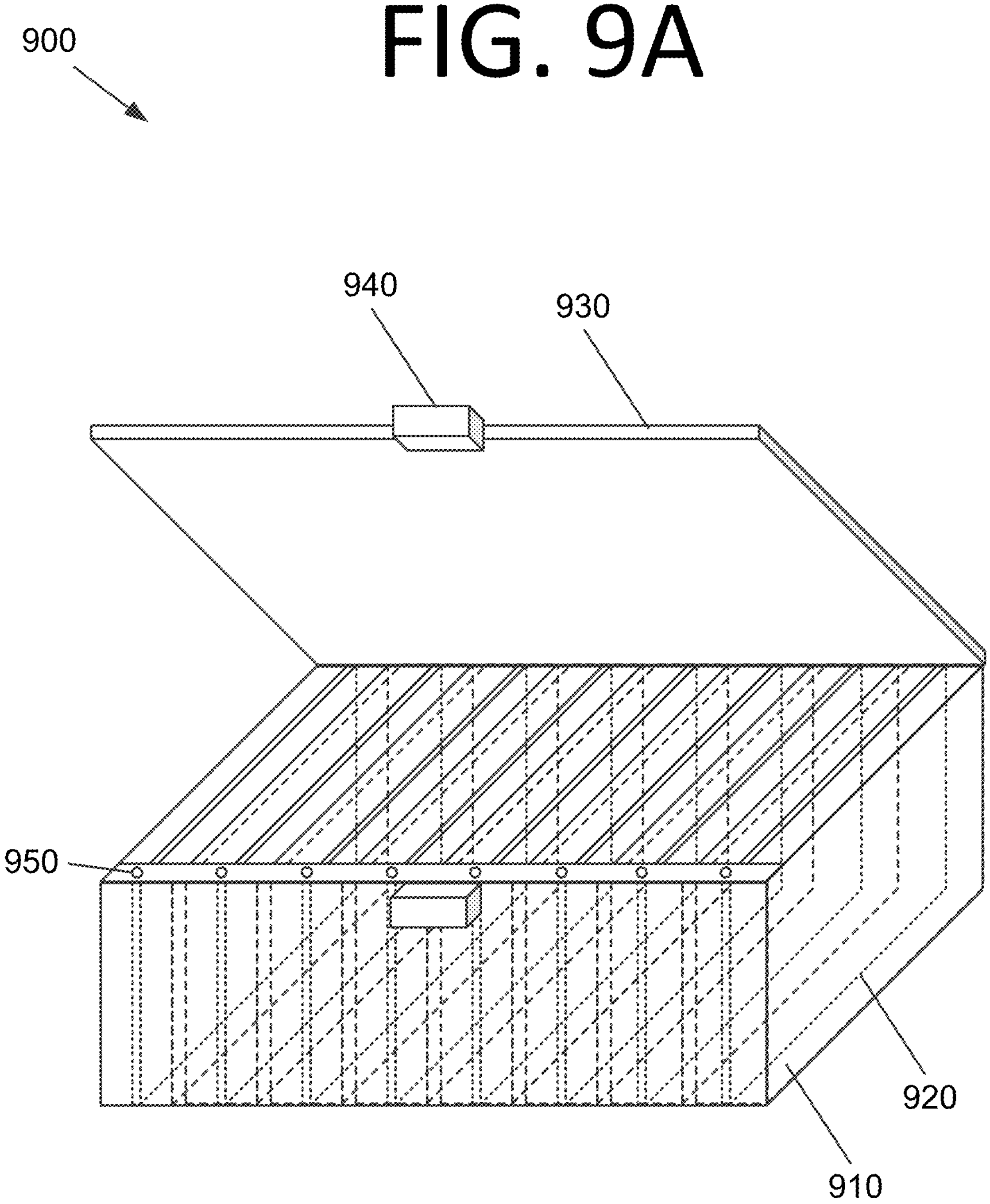
FIG. 9A is a perspective view illustrating a tray, according to an embodiment of the present invention.
Figure 9B:
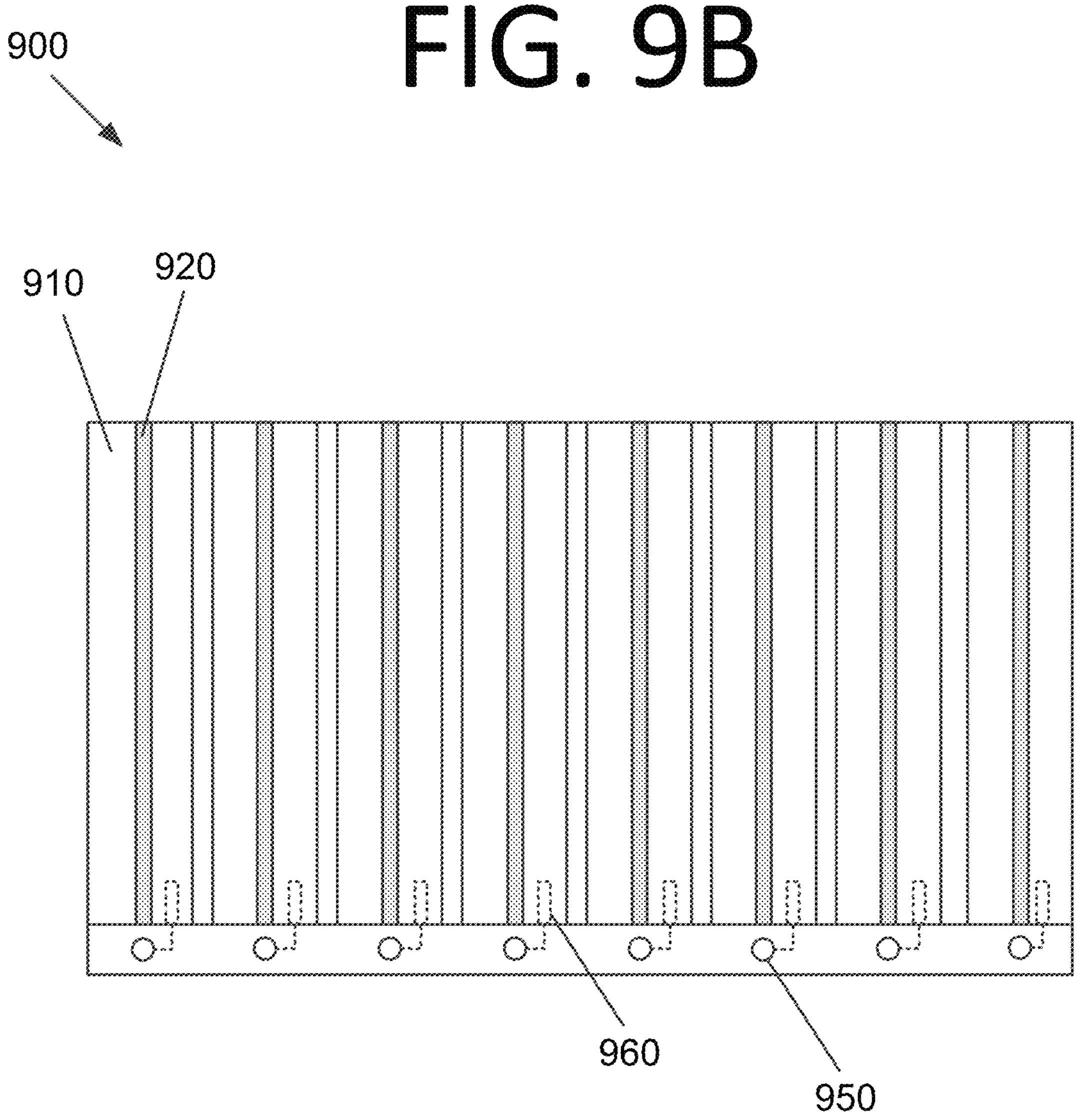
FIG. 9B is a top view illustrating the tray of FIG. 9A with the cover, hinges, and lock removed, according to an embodiment of the present invention.
Figure 9C:
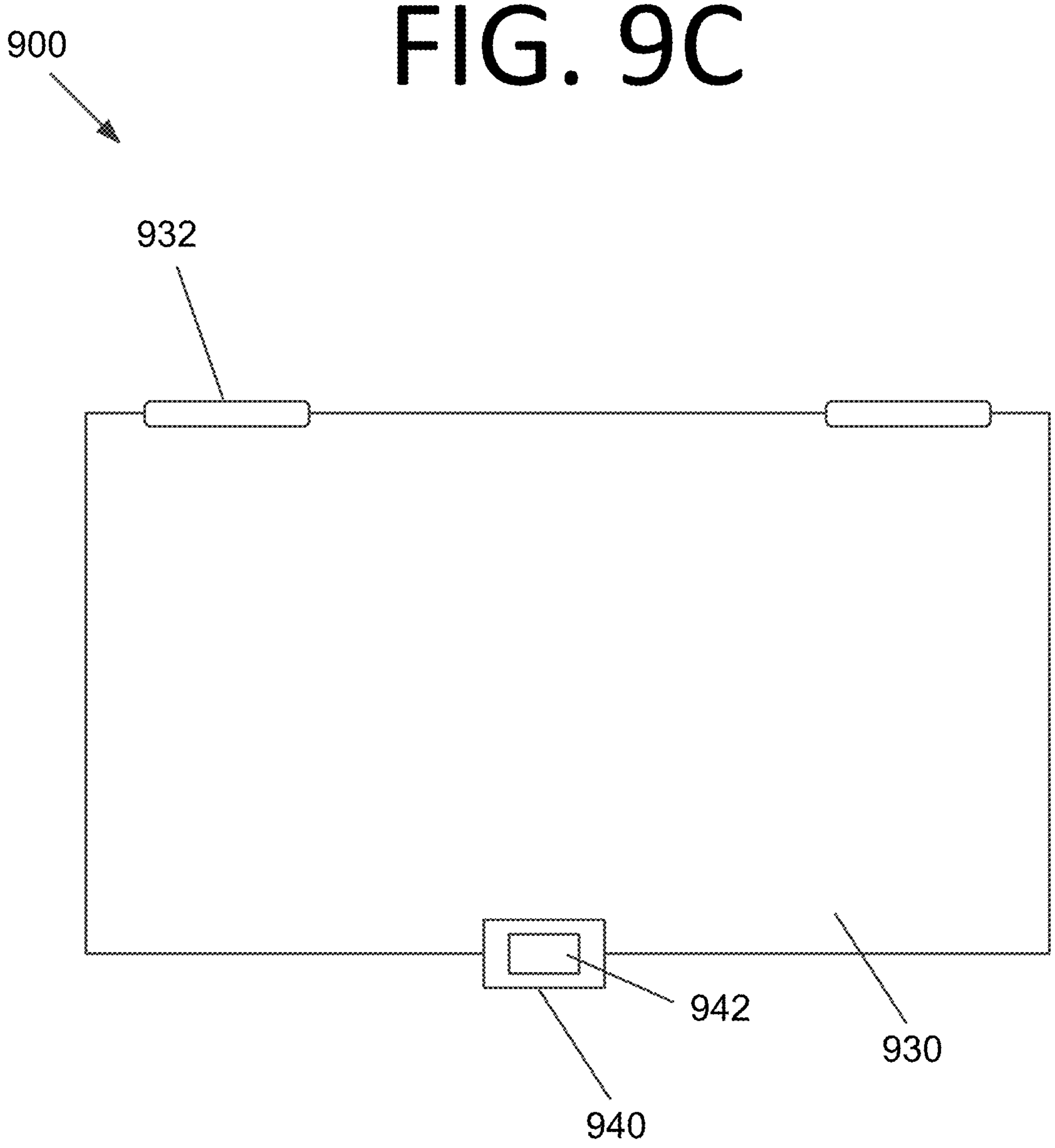
FIG. 9C is a top view illustrating the tray of FIG. 9A with the cover closed, according to an embodiment of the present invention.

FIGS. 9A-C illustrate a tray 900, according to an embodiment of the present invention. Tray 900 includes multiple compartments 910, each of which stores a populated blister card 920. Tray 900 is hinged with a cover 930 and hinges 932. Cover 930 locks via a lock 940 that requires an ID to open. The ID may be a numerical code, a fingerprint scan, etc., depending on the mechanism used by lock 940. In this embodiment, lock 940 includes a fingerprint scanner 942. Instead of delivering a package containing hundreds of individual loose pills, for example, tray 900 stores a respective blister card 920 in each compartment 910.

Blister cards 920 may be in an additional casing for ease of management in some embodiments. Each compartment 910 of tray 900 is numbered in some embodiments and has an associated indicator (here, a light 950) that connects with a contact point 960 of each compartment that makes contact with corresponding a contact point on a harness of a drawer that is configured to be aligned with a contact point on tray 900. See FIG. 10, for example. Tray 900 is placed within a drawer type harness of a cabinet that has contact points aligned with each compartment. The harness has an electrical contact with the cabinet. Each tray 900 and harness are connected to a wireless module of the cabinet. The location of each harness of a multiple harness cabinet is stored in a database. The cabinet has wireless connectivity to computing systems of a pharmacy. Each compartment 910 also has a sensor or switch (not shown) that detects the presence/removal of blister card 920 from compartment. The sensor or switch may be similar to those described elsewhere herein.

Tray 900 is delivered to the pharmacy from the manufacturer. It should be noted that any desired number of compartments and blister cards of any desired size and number of doses may be accommodated without deviating from the scope of the invention. In some embodiments, tray 900 does not require modifications to existing blister cards provided by manufacturers.

Figure 10A:
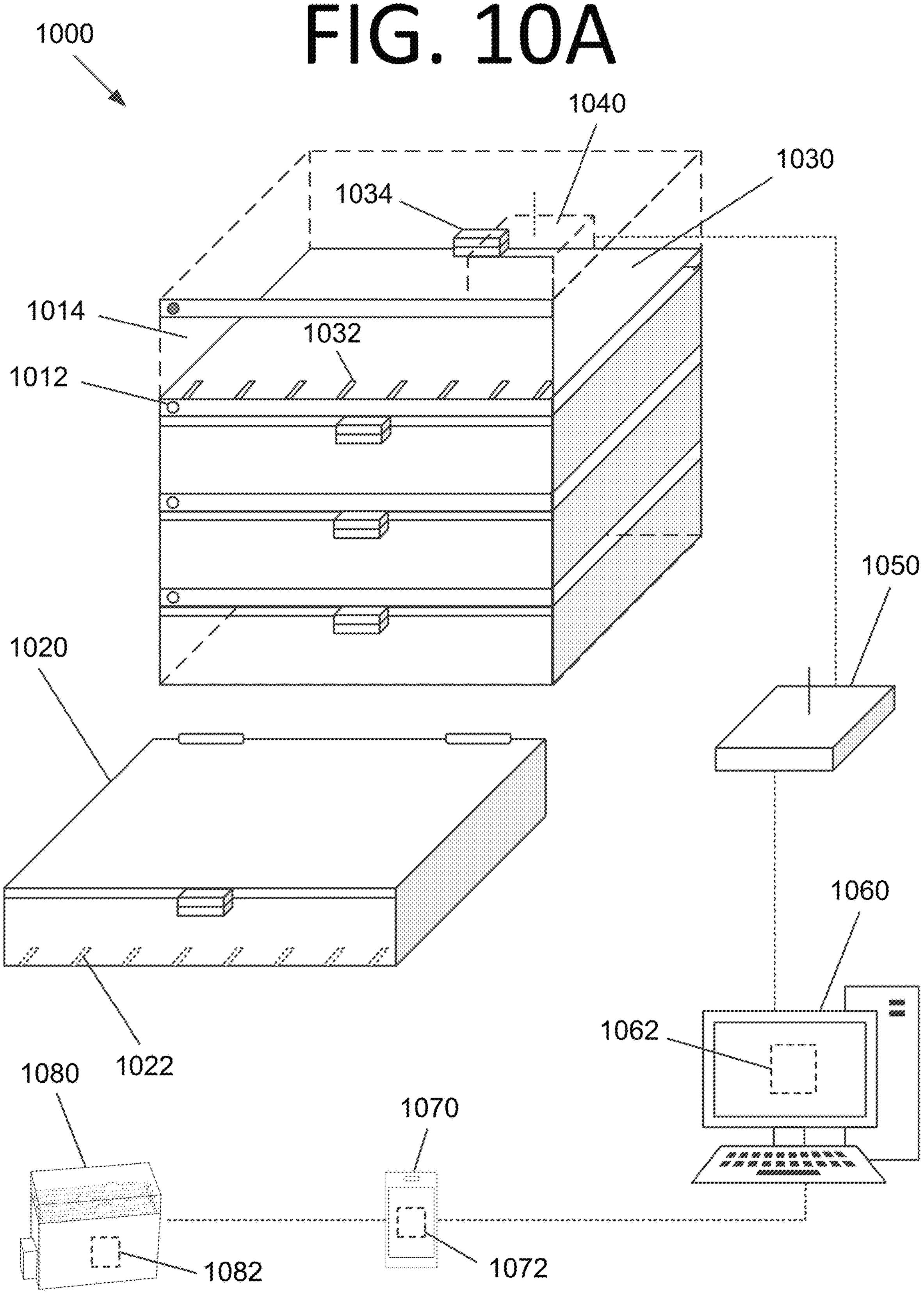
FIG. 10A illuis a perspective view illustrating a cabinet system with the cabinet shown transparently, according to an embodiment of the present invention.
Figure 10B:
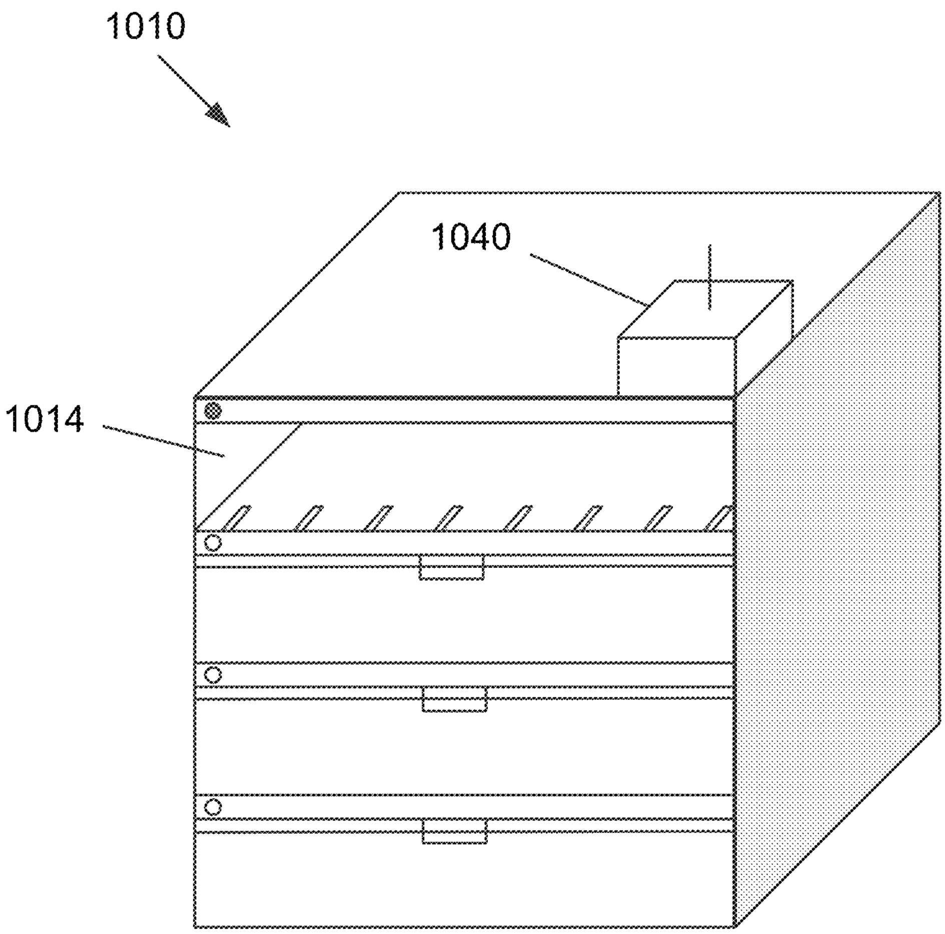
FIG. 10B is a perspective view illustrating the cabinet of FIG. 10A, according to an embodiment of the present invention.

FIG. 10A illustrates a cabinet system 1000 and FIG. 10B illustrates a cabinet 1010, according to an embodiment of the present invention. A cabinet 1010 is synchronized with pharmacy software so that when a tray 1020 is delivered and scanned, a light 1012 indicates the location where new tray 1020 should be placed. In some embodiments, tray 1020 may be tray 900 of FIGS. 9A-C. Light 1012 goes out when tray 1020 is inserted in a harness 1030 and a recess 1014, pushed in and automatically locked via lock 1034. This may occur responsive to contacts 1032 of harness 1030 contacting respective contacts 1022 of tray 1020. A computing system 1040 of cabinet 1010 then sends a message to a software application 1062 running on a pharmacy computing system 1060 via a wireless router/modem 1050. Software application 1062 logs the location of tray 1020 (e.g., in a database (not shown)) and knows the location and contents of each blister card in tray 1020.

A manufacturer may pack and seal a tray 1020 with pill blister cards after having assigned a barcode or chip that records the contents of tray 1020. Tray 1020 is delivered to a pharmacy when supplies are requested. Tray 1020 is scanned and logged into software application 1062 at the pharmacy via computing system 1060 and then placed into cabinet 1010. All authentication of product and contents are done automatically in some embodiments.

When a prescription is to be filled, a pharmacist or other authorized user log into software application 1062 and the patient's account. The pharmacist then unlocks a respective tray 1020 from cabinet 1010. Tray 1020 is pulled out and the locked cover of tray 1020 is then opened. It should be noted that in some embodiments, however, a cover is not present. The blister card that has an active light in tray 1020 is then selected and removed as instructed by software application 1062. The blister card is removed from its container, if included, and the container is replaced into tray 1020 or discarded. The cover is then re-locked and tray 1020 is pushed back into the cabinet 1010 and locked in place. In some embodiments, trays 1020 may be reused to reduce cost and the effect on the environment.

The blister card is labeled, scanned, and placed into a patient's medication magazine 1080. See FIGS. 1A-L, for example. Actions for the card with respect to tray 1020 are automatically recorded via software application 1062. Forced access to tray 1020 may set off multiple alarms in some embodiments via computing systems 1040, 1060 and software application 1062.

A patient may use medication magazine 1080 as disclosed in the subject application. In some embodiments, the patient is notified via a software application 1072 on a mobile device 1070 when it is time to take a dose of the medication. The removal of a pill is noted via a software application 1082 on medication magazine 1080 and automatically logged into the patient account via the mobile device 1070 and software application 1062. Tray 1020 and harness 1030 may be optimized to work with medication magazine 10080 for the tracking of individual pills, including both retail and hospital pharmacies. However, it should be noted that such a system may also be useful in the management of general pharmacy inventory for ordinary containers that do not require the precision of coordinating with a blister card magazine. A pharmacist can quickly locate and manage containers of drugs with a system that automatically updates in this manner.

Much of dispensing relates to accurately communicating with patients, including the printing of labels and papers outlining instructions. This is cumbersome for both pharmacists and patients and lacks the efficiency of a modern digital approach that reduces stress and improves accuracy and accountability. The software application of managing trays, cabinets, harnesses, and magazines streamlines, simplifies, and automates this process.

The connecting of blister card trays and magazines to online monitoring creates a new category of telehealth accessibility, as well as a new IoT device. The magazine can be wearable and may have a belt, holster, clip, or some other attachment mechanism to secure the medication magazine to the patient's body for security and to facilitate medication access and adherence by the patient. See FIG. 1J, for example.

Manufacturers can be updated with respect to the real time or near-real time use of their medication in the possession of patients. This also provides the potential for efficient step treatment and real time intervention, when necessary. The misuse of certain drugs, such as opiates, requires immediate and urgent medical attention. Such embodiments can thus lead to better pharmacy performance, better patient care, and saved lives by providing accountability with respect to the potentially destructive misuse of drugs.

In an embodiment, a medication management system includes one or more trays. The one or more trays include a plurality of compartments. Each compartment of the one or more trays is configured to store a respective blister card and includes a sensor or switch. The one or more trays also include an indicator for each compartment in the one or more trays and a contact point for each compartment in the one or more trays. However, in some embodiments fewer contact points (or even one) may be used.

The medication management system also includes a cabinet that includes a plurality of indicators for each of the one or more trays and a plurality of recesses for each of the one or more trays. The cabinet also includes a plurality of harnesses located in respective recesses of the plurality of recesses. The plurality of harnesses include a plurality of contact points for each contact point of the one or more trays. The plurality of contact points of the harness are configured to align with the respective contact points of the one or more trays when a respective tray of the one or more trays is inserted into the cabinet. In some embodiments, the one or more trays include a lid operably connected to an upper part of the tray and a lock operably connected to a lid and the tray.

In some embodiments, the medication management system includes a cabinet computing system including memory storing computer program instructions and at least one processor configured to execute the computer program instructions. The computer program instructions are configured to cause the at least one processor to track insertion and removal of the one or more trays into and out of the cabinet, initiate a respective indicator for a tray of the one or more trays or a compartment of a tray of the one or more trays, and stop the respective indicator for the tray of the one or more trays or the compartment of the tray of the one or more trays responsive to the tray being placed in the cabinet or a blister card being removed from the compartment. In certain embodiments, the computer program instructions of the cabinet computing system are further configured to cause the at least one processor to determine that a tray of the one or more trays has been removed or a compartment of the tray has been opened without authorization and send an alert to another computing system indicating that improper access has occurred. In some embodiments, the computer program instructions of the cabinet computing system are further configured to cause the at least one processor to communicate updates for the cabinet and the one or more trays to pharmacy management software.

In some embodiments, the medication management system includes a pharmacy computing system that includes memory storing computer program instructions and at least one processor configured to execute the computer program instructions. The computer program instructions are configured to cause the at least one processor to unlock a tray of the one or more trays from the cabinet via the cabinet computing system, track removal of the tray from the cabinet, track return of the tray to the cabinet, and confirm that a blister sleeve was removed from an appropriate compartment. In certain embodiments, the computer program instructions of the pharmacy computing system are further configured to cause the at least one processor to generate an alert responsive to the tray not being replaced within a period of time or a blister sleeve being removed from an incorrect compartment.

In some embodiments, the medication management system includes a medication magazine and a mobile device. The mobile device is configured to inform a user that a dose of a medication should be taken. The medication magazine is configured to track access to and removal of a dose from a blister card stored in the medication magazine and confirm whether an appropriate dose was taken and inform the mobile device. The mobile device is also configured to inform the pharmacy computing system of a status of the dose. In certain embodiments, the mobile device is configured to alert the user when the dose was not taken correctly. In some embodiments, the medication magazine is portable. In certain embodiments, the medication magazine includes an attachment mechanism and is wearable.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A medication management system, comprising:

one or more trays, comprising:

a plurality of compartments, each compartment of the one or more trays configured to store a respective blister card and comprising a sensor or switch, an indicator for each compartment in the one or more trays, and a contact point for each compartment in the one or more trays; and a cabinet, comprising:

a plurality of indicators for each of the one or more trays, a plurality of recesses for each of the one or more trays, a plurality of harnesses located in respective recesses of the plurality of recesses, the plurality of harnesses comprising a plurality of contact points for each contact point of the one or more trays, the plurality of contact points of the harness configured to align with the respective contact points of the one or more trays when a respective tray of the one or more trays is inserted into the cabinet.

2. The medication management system of claim 1, wherein the one or more trays comprise:

a lid operably connected to an upper part of the tray; and a lock operably connected to a lid and the tray.

3. The medication management system of claim 1, further comprising:

a cabinet computing system comprising memory storing computer program instructions and at least one processor configured to execute the computer program instructions, wherein the computer program instructions are configured to cause the at least one processor to:

track insertion and removal of the one or more trays into and out of the cabinet, initiate a respective indicator for a tray of the one or more trays or a compartment of a tray of the one or more trays, and stop the respective indicator for the tray of the one or more trays or the compartment of the tray of the one or more trays responsive to the tray being placed in the cabinet or a blister card being removed from the compartment.

4. The medication management system of claim 3, wherein the computer program instructions of the cabinet computing system are further configured to cause the at least one processor to:

determine that a tray of the one or more trays has been removed or a compartment of the tray has been opened without authorization; and send an alert to another computing system indicating that improper access has occurred.

5. The medication management system of claim 3, wherein the computer program instructions of the cabinet computing system are further configured to cause the at least one processor to:

communicate updates for the cabinet and the one or more trays to pharmacy management software.

6. The medication management system of claim 3, further comprising:

a pharmacy computing system comprising memory storing computer program instructions and at least one processor configured to execute the computer program instructions, wherein the computer program instructions are configured to cause the at least one processor to:

unlock a tray of the one or more trays from the cabinet via the cabinet computing system, track removal of the tray from the cabinet, track return of the tray to the cabinet, and confirm that a blister sleeve was removed from an appropriate compartment.

7. The medication management system of claim 6, wherein the computer program instructions of the pharmacy computing system are further configured to cause the at least one processor to:

generate an alert responsive to the tray not being replaced within a period of time or a blister sleeve being removed from an incorrect compartment.

8. The medication management system of claim 6, further comprising:

a medication magazine; and a mobile device, wherein the mobile device is configured to inform a user that a dose of a medication should be taken, the medication magazine is configured to track access to and removal of a dose from a blister card stored in the medication magazine, the medication magazine is configured to confirm whether an appropriate dose was taken and inform the mobile device, and the mobile device is configured to inform the pharmacy computing system of a status of the dose.

9. The medication management system of claim 8, wherein the mobile device is configured to alert the user when the dose was not taken correctly.

10. The medication management system of claim 8, wherein the medication magazine is portable.

11. The medication management system of claim 10, wherein the medication magazine comprises an attachment mechanism and is wearable.

12. A medication management system, comprising:

one or more trays, comprising:

a plurality of compartments, each compartment of the one or more trays configured to store a respective blister card and comprising a sensor or switch, an indicator for each compartment in the one or more trays, and a contact point for each compartment in the one or more trays;

a cabinet, comprising:

a plurality of indicators for each of the one or more trays, a plurality of recesses for each of the one or more trays, a plurality of harnesses located in respective recesses of the plurality of recesses, the plurality of harnesses comprising a plurality of contact points for each contact point of the one or more trays, the plurality of contact points of the harness configured to align with the respective contact points of the one or more trays when a respective tray of the one or more trays is inserted into the cabinet;

a cabinet computing system;

a pharmacy computing system;

a medication magazine; and a mobile device, wherein the mobile device is configured to inform a user that a dose of a medication should be taken, the medication magazine is configured to track access to and removal of a dose from a blister card stored in the medication magazine, the medication magazine is configured to confirm whether an appropriate dose was taken and inform the mobile device, and the mobile device is configured to inform the pharmacy computing system of a status of the dose.

13. The medication management system of claim 12, wherein the cabinet computing system comprises memory storing computer program instructions and at least one processor configured to execute the computer program instructions, the computer program instructions configured to cause the at least one processor to:

track insertion and removal of the one or more trays into and out of the cabinet;

initiate a respective indicator for a tray of the one or more trays or a compartment of a tray of the one or more trays;

stop the respective indicator for the tray of the one or more trays or the compartment of the tray of the one or more trays responsive to the tray being placed in the cabinet or a blister card being removed from the compartment; and communicate updates for the cabinet and the one or more trays to the pharmacy computing system.

14. The medication management system of claim 12, wherein the pharmacy computing system comprises memory storing computer program instructions and at least one processor configured to execute the computer program instructions, the computer program instructions configured to cause the at least one processor to:

unlock a tray of the one or more trays from the cabinet via the cabinet computing system;

track removal of the tray from the cabinet;

track return of the tray to the cabinet; and confirm that a blister sleeve was removed from an appropriate compartment.

15. The medication management system of claim 12, wherein the medication magazine is portable.

16. The medication management system of claim 15, wherein the medication magazine comprises an attachment mechanism and is wearable.

17. A medication management system, comprising:

one or more trays, comprising:

a plurality of compartments, each compartment of the one or more trays configured to store a respective blister card and comprising a sensor or switch, an indicator for each compartment in the one or more trays, and at least one contact point on the one or more trays;

a cabinet, comprising:

a plurality of indicators for each of the one or more trays, a plurality of recesses for each of the one or more trays, a plurality of harnesses located in respective recesses of the plurality of recesses, the plurality of harnesses comprising at least one respective contact point for each contact point of the one or more trays, the at least one contact point of the harness configured to align with the respective at least one contact point of the one or more trays when a respective tray of the one or more trays is inserted into the cabinet; and a cabinet computing system configured to track statuses of the cabinet.

18. The medication management system of claim 17, wherein the cabinet computing system comprises memory storing computer program instructions and at least one processor configured to execute the computer program instructions, the computer program instructions configured to cause the at least one processor to:

track insertion and removal of the one or more trays into and out of the cabinet;

initiate a respective indicator for a tray of the one or more trays or a compartment of a tray of the one or more trays; and stop the respective indicator for the tray of the one or more trays or the compartment of the tray of the one or more trays responsive to the tray being placed in the cabinet or a blister card being removed from the compartment.

19. The medication management system of claim 17, wherein the computer program instructions of the cabinet computing system are further configured to cause the at least one processor to:

determine that a tray of the one or more trays has been removed or a compartment of the tray has been opened without authorization; and send an alert to another computing system indicating that improper access has occurred.

20. The medication management system of claim 17, wherein the computer program instructions of the cabinet computing system are further configured to cause the at least one processor to:

communicate updates for the cabinet and the one or more trays to pharmacy management software.

* * * * *